United States Patent [19]
Yano et al.

[11] Patent Number: 5,521,202
[45] Date of Patent: May 28, 1996

[54] THIAZOLIDINE DERIVATIVES AND PHARMACEUTICAL COMPOSITIONS CONTAINING THE SAME

[75] Inventors: Shingo Yano, Kawagoe; Kazuo Ogawa, Tokushima; Masakazu Fukushima, Hannou, all of Japan

[73] Assignee: Taiho Pharmaceutical Co., Ltd., Tokyo, Japan

[21] Appl. No.: 351,260

[22] PCT Filed: Apr. 7, 1994

[86] PCT No.: PCT/JP94/00590

§ 371 Date: Dec. 6, 1994

§ 102(e) Date: Dec. 6, 1994

[87] PCT Pub. No.: WO94/22857

PCT Pub. Date: Oct. 13, 1994

[30] Foreign Application Priority Data

Apr. 7, 1993 [JP] Japan ..................... 5-080846

[51] Int. Cl.$^6$ ............ C07D 417/12; A61K 31/425
[52] U.S. Cl. .............. 514/369; 544/322; 546/269.7; 546/270.7; 546/271.4; 548/183
[58] Field of Search ..................... 548/183, 280; 544/322; 514/364

[56] References Cited

FOREIGN PATENT DOCUMENTS

| 295828 | 12/1988 | European Pat. Off. . |
| 306228 | 3/1989 | European Pat. Off. . |
| 356214 | 2/1990 | European Pat. Off. . |

*Primary Examiner*—Robert Gerstl
*Attorney, Agent, or Firm*—Sughrue, Mion, Zinn, Macpeak & Seas

[57] ABSTRACT

A thiazolidine derivative represented by the following formula (1):

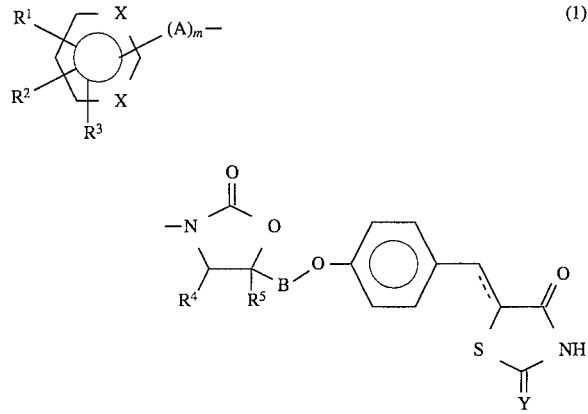

X represents a carbon atom or nitrogen atom, Y represents an oxygen atom or an imino group; A and B individually represent a lower alkylene group, m stands for 0 or 1, and a method of treatment of diabetes by administration of the compound.

6 Claims, No Drawings

THIAZOLIDINE DERIVATIVES AND PHARMACEUTICAL COMPOSITIONS CONTAINING THE SAME

This application is a 371 of PCT/JP94/00590 filed 4/7/94.

TECHNICAL FIELD

The present invention relates to novel thiazolidine derivatives and salts thereof. More specifically, this invention relates to thiazolidine derivatives or salts thereof which have blood-sugar lowering action and blood-lipid lowering action and are useful as hypoglycemic agents and anti-hyperlipidemia agents, preparation processes thereof, pharmaceutical compositions containing one or more of the compounds and therapeutic methods for diabetes.

BACKGROUND ART

As synthetic therapeutic agents for diabetes which show blood-sugar lowering action, sulfonylurea preparations have commonly been used to date. Their use, however, requires very careful control because they may cause hypoglycemic symptoms or induce drug resistance. In recent years, development of hypoglycemic agents is therefore under way as substitutes for the above sulfonyl urea preparations. Among them, interested are those capable of enhancing the insulin sensitivity at peripheries and showing blood-sugar lowering action., Effects available from these agents, however, are still not satisfactory and moreover, their side effects cannot be considered to have been reduced fully. Further, as there are many diabetics who have also developed hyperlipidemia, there is an outstanding demand for the development of pharmaceuticals having both blood-sugar lowering action and blood-lipid lowering action.

DISCLOSURE OF THE INVENTION

In view of the foregoing circumstances, the present inventors have carried out an extensive investigation. As a result, it has been found that certain novel, specific thiazolidine derivatives and salts thereof have both the above actions, leading to the completion of the invention.

The present invention therefore provides a thiazolidine derivative represented by the following formula (1):

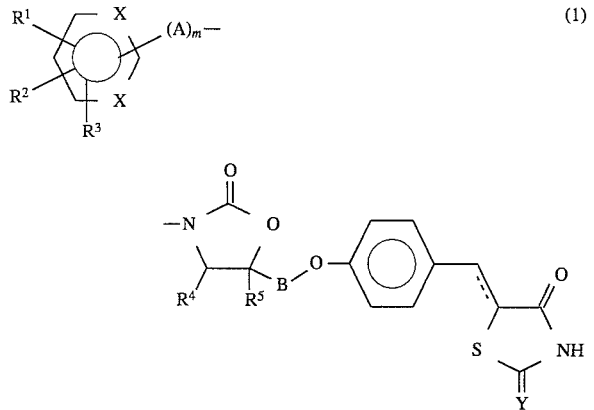

wherein $R^1$, $R^2$ and $R^3$ may be the same or different and individually represent a hydrogen atom, a halogen atom, a lower alkyl group or lower alkoxyl group which may be substituted by one or more halogen atom(s), a hydroxyl group, a nitro group, an amino group, a lower acylamino group, a mono- or di-lower alkylamino group, a carboxyl group, a lower alkoxycarbonyl group, a cyano group, a 2-oxazolyl group, a thiazolidine-2,4-dion-5-ylidene-methyl group or a thiazolidine-2,4-dion-5-ylmethyl group and $R^1$ and $R^2$ may be coupled together to form an alkylene chain $-(CH_2)_p-$ wherein p stands for 3, 4 or 5 or an alkylenedioxy chain $-O(CH_2)_qO-$ wherein q stands for 1, 2 or 3, thereby forming a ring; $R^4$ and $R^5$ may be the same or different and individually represent a hydrogen atom or a lower alkyl group; X represents a carbon atom or nitrogen atom; Y represents an oxygen atom or an imino group; A and B individually represent a lower alkylene group; m stands for 0 or 1; and the dashed line indicates the presence or absence of a double bond; or a salt thereof and a preparation process thereof.

In addition, the present invention provides a pharmaceutical composition which comprises an effective amount of the thiazolidine derivative (1) or a salt thereof and a pharmacologically acceptable carrier.

Further, the present invention provides a method of treatment of diabetes which comprises administering to patients an effective amount of the thiazolidine derivative (1) or a salt thereof.

Each thiazolidine derivative or a salt thereof according to the present invention has excellent blood-sugar lowering action and blood-lipid lowering action. It has good absorption into the body and has long lasting drug efficacy. In addition, it has excellent excretion and low toxicity against the human body, so that it is useful as pharmaceuticals such as a diabetes treating agent, a hyperlipidemia treating agent, an arteriosclerosis preventive and treating agent, and an obesity preventive drug.

BEST MODES FOR CARRYING OUT THE INVENTION

The thiazolidine derivatives represented by the formula (1) have optical isomers. It is to be noted that these optical isomers are all embraced by the present invention.

In the formula (1), examples of the halogen atoms represented by $R^1$, $R^2$ and $R^3$ include fluorine, chlorine, bromine and iodine atoms.

In the formula (1), examples of the lower alkyl groups represented by $R^1$, $R^2$ and $R^3$ include linear or branched $C_{1-6}$ alkyl groups such as methyl, ethyl, n-propyl, isopropyl, n-butyl, isobutyl, sec-butyl, tert-butyl, pentyl and hexyl.

Illustrative examples of the halogen-containing lower alkyl group include linear or branched $C_{1-6}$ alkyl groups containing 1–3 halogen atoms such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2-trichloroethyl, 3-fluoropropyl, 3,3,3-trichloropropyl, 4-chlorobutyl, 5-chloropentyl, 6-chlorohexyl and 3-chloro-2-methylpropyl.

Exemplary lower alkoxyl groups include linear or branched $C_{1-6}$ alkoxyl groups such as methoxy, ethoxy, n-propoxy, isopropoxy, n-butoxy, isobutoxy, sec-butoxy, tert-butoxy, n-pentyloxy, isopentyloxy and n-hexyloxy.

Illustrative examples of the halogen-containing lower alkoxyl group include linear or branched $C_{1-6}$ alkoxyl groups containing 1–3 halogen atoms such as chloromethoxy, bromomethoxy, iodomethoxy, fluoromethoxy, dichloromethoxy, dibromomethoxy, difluoromethoxy, trichloromethoxy, tribromomethoxy, trifluoromethoxy, 2-chloroethoxy, 2-bromoethoxy, 2-fluoroethoxy, 1,2-dichloroethoxy, 2,2-difluoroethoxy, 1-chloro-2-fluoroethoxy, 2,2,2-trifluoroethoxy, 2,2,2-trichloroethoxy, 3-fluoropropoxy, 3,3,3-trichloro-propoxy, 4-chlorobutoxy, 5-chloropentyloxy, 6-chlorohexyloxy and 3-chloro-2-methylpropyloxy.

Examples of the lower acylamino group include linear or branched $C_{2-6}$ acylamino groups such as acetylamino, propanoylamino, butanoylamino, 2-methylpropanoylamino, valerylamino and hexanoylamino.

Examples of the mono- or di-lower alkylamino group include those containing any one of the above-exemplified lower alkyl groups substituted for one of the hydrogen atoms of the amino group and those containing any two of these lower alkyl groups, which may be the same or different, substituted for two of the hydrogen atoms of the amino group, respectively.

Examples of the lower alkoxycarbonyl group include those having carboxyl groups esterified by any one of the above-exemplified lower alkyl group.

Illustrative examples of the lower alkyl group represented by $R^4$ or $R^5$ include linear or branched $C_{1-6}$ alkyl groups such as methyl, ethyl, n-propyl, isopropyl, n-butyl, isobutyl, sec-butyl, tert-butyl, pentyl and hexyl. It is desired that either or both of $R^4$ and $R^5$ be hydrogen atoms. Y represents an oxygen atom or an imino group, with an oxygen atom being preferred.

Examples of the lower alkylene group represented by A or B include linear or branched $C_{1-4}$ alkylene groups such as methylene, ethylene, trimethylene, tetramethylene, methylmethylene and 2-methyltrimethylene. As B, methylene and ethylene are preferred.

Although m stands for 0 or 1, 0 is preferred.

The preferred examples of the thiazolidine derivative (1) according to the present invention are those in which $R^1$, $R^2$ and $R^3$ individually represent a hydrogen atom, a halogen atom, a lower alkyl group, a trifluoromethyl group, a lower alkoxyl group, a trifluoromethoxy group, a hydroxyl group, a nitro group, an amino group, an acetylamino group, a dimethylamino group, a carboxyl group, an ethoxycarbonyl group, a cyano group, a 2-oxazolyl group, a thiazolidine-2,4-dion- 5-ylidenemethyl group or a thiazolidine-2,4-dion-5-ylmethyl group and $R^1$ and $R^2$ may be coupled together to form a trimethylene, methylene dioxy or ethylene dioxy group, thereby forming a ring; $R^4$ and $R^5$ individually represents a hydrogen atom or a methyl group; and A and B individually represents a methylene or ethylene group.

The more preferred examples of the thiazolidine derivative (1) include the above-described preferred compounds in which B represents a methylene or ethylene group, m stands for 0 and $R^4$ and $R^5$ individually represent a hydrogen atom and Y is an oxygen atom.

The particularly preferred examples of the thiazolidine derivative (1) include the above-described more preferred compounds in which $R^1$, $R^2$ and $R^3$ individually represent a hydrogen atom, a halogen atom, a lower alkyl group, a trifluoromethyl group, a lower alkoxyl group or a trifluoromethoxy group.

Specific examples of the particularly preferred thiazolidine derivative (1), for instance, include following compounds.

5-{4-[3-(4-methoxyphenyl)-2-oxooxazolidin-5-yl]-methoxy}benzyl- 2,4-thiazolidinedione 5-{4-[3-(3,4-difluorophenyl)-2-oxooxazolidin-5-yl]-methoxy}benzyl- 2,4-thiazolidinedione 5-{4-[3-(4-chloro-2-fluorophenyl)-2-oxooxazolidin-5-yl]methoxy}benzyl-2,4-thiazolidinedione 5-{4-[3-(4-trifluoromethoxyphenyl)-2-oxooxazolidin-5-yl]methoxy}benzyl-2,4-thiazolidinedione 5-{4-[3-(4-trifluoromethylphenyl)-2-oxooxazolidin- 5-yl]methoxy}benzyl-2,4-thiazolidinedione 5-{4-{2-[3-(4-trifluoromethylphenyl)-2-oxooxazolidin-5-yl]ethoxy}benzyl}-2,4-thiazolidinedione 5-{4-{2-[3-(4-chloro-2-fluorophenyl)-2-oxooxazolidin-5-yl]ethoxy}benzyl}-2,4-thiazolidinedione 5-{4-[3-(4-pyridyl)-2-oxooxazolidin-5-yl]methoxy}-benzyl- 2,4-thiazolidinedione Illustrative of the salts of the thiazolidine derivative (1) according to the present invention include acid-addition salts and base salts which have been obtained by causing pharmacologically acceptable acids and basic compounds to act on the derivative, respectively. Examples of the acid addition salts include salts of a thiazolidine derivative (1), especially a compound containing a basic group such as an amino group or mono- or di-lower alkyl amino group with an acid such as an inorganic acid, e.g., hydrochloric acid, sulfuric acid, phosphoric acid or hydrobromic acid or an organic acid, e.g., oxalic acid, maleic acid, fumaric acid, malic acid, tartaric acid, citric acid, benzoic acid, acetic acid, p-toluenesulfonic acid or ethanesulfonic acid. Exemplary base salts include salts with an alkali metal or alkaline earth metal such as sodium, potassium, magnesium or calcium and organic salts with an amine such as ammonia, methylamine, dimethylamine, piperidine, cyclohexylamine or triethylamine.

The thiazolidine derivatives of the present invention represented by the formula (1) can be prepared, for instance, in accordance with Process A, Process B or Process C using various compounds as raw materials:

Process A:

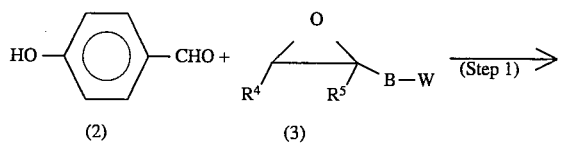

(2)   (3)

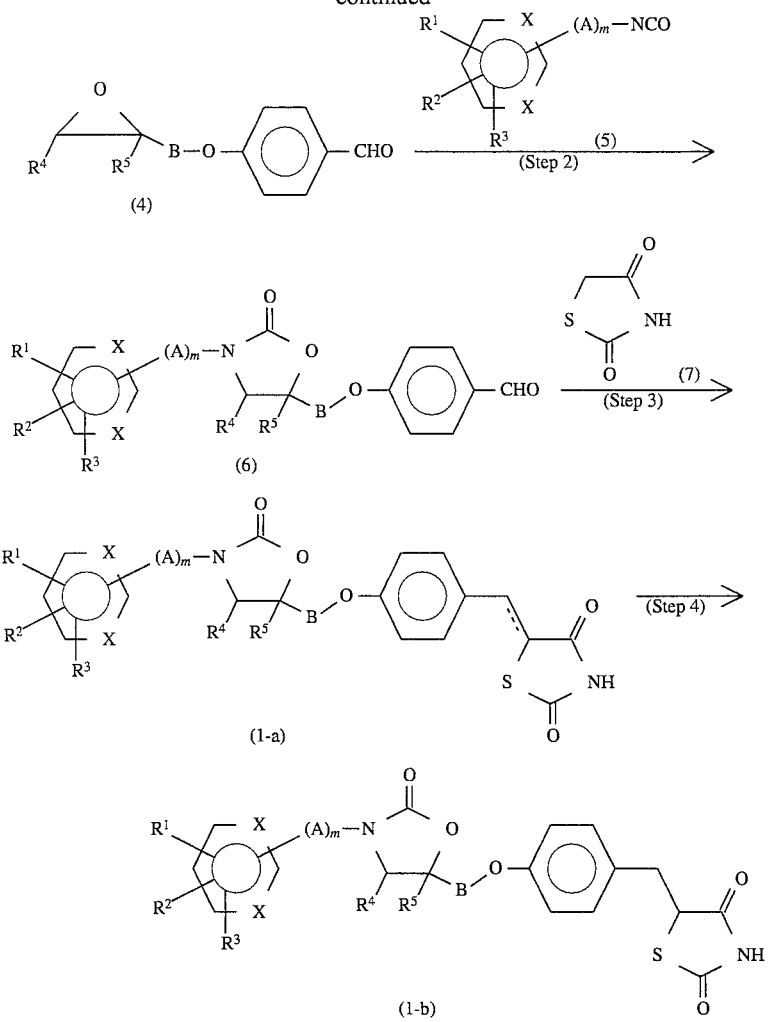

wherein W represents a halogen atom, a lower alkanesulfonyloxy group which may contain one or more substituent(s), or a lower arylsulfonyloxy group which may contain one or more substituent(s); and $R^1$, $R^2$, $R^3$, $R^4$, $R^5$, A, B, X, m and the dashed line have the same meanings as described above.

In the compound represented by the formula (3), examples of the halogen atom represented by W include, fluorine, chlorine, bromine and iodine atoms. Examples of the substituted or unsubstituted lower alkanesulfonyloxy group include $C_{1-6}$ alkanesulfonyloxy groups, which may be substituted or unsubstituted by one or more halogen atom(s), such as methanesulfonyloxy, ethanesulfonyloxy, propanesulfonyloxy and trifluoro-methanesulfonyloxy. Examples of the substituted or unsubstituted lower arylsulfonyloxy group include arylsulfonyloxy groups, which may be substituted or unsubstituted by one or more $C_{1-6}$ alkyl group(s), halogen atom(s) and/or nitro group(s), such as benzenesulfonyloxy, toluenesulfonyloxy, p-chlorobenzenesulfonyloxy and m-nitrobenzenesulfonyloxy.

The above steps 1–4 can be conducted as follows:
(Step 1)

The compounds represented by the formula (4), which include novel compounds, can each be prepared usually by reacting p-hydroxybenzaldehyde (2) with a known compound represented by the formula (3) [Chemical Reviews, 91, 437(1991)] in a suitable solvent in the presence of a basic compound.

No particular limitation is imposed on the solvent insofar as it takes no part in the reaction. Examples of the solvent include ethers such as diethyl ether, tetrahydrofuran and dioxane; halogenated hydrocarbons such as dichloromethane and chloroform; amines such as pyridine, piperidine and triethylamine; alkylketones such as acetone, methyl ethyl ketone and methyl isobutyl ketone; alcohols such as methanol, ethanol and propanol; aprotic polar solvents such as N,N-dimethylformamide, N,N-dimethylacetamide, acetonitrile, dimethyl sulfoxide and hexamethylphosphoric triamide.

Illustrative basic compounds include organic, basic compounds such as tertiary amines, e.g., triethylamine and pyridine; and inorganic basic compounds such as alkali metal carbonates, e.g., sodium carbonate and potassium carbonate, alkali metal bicarbonates such as sodium bicarbonate and potassium bicarbonate, alkali metal hydroxides, e.g., sodium hydroxide and potassium hydroxide, alkali metals, e.g., sodium and potassium, and alkali metal hydrides, e.g., sodium hydride. Upon reaction, the compound of the formula (3) may be used in an amount of 1–2 mole equivalents and the basic compound in an amount of 1–10 mole equivalents, preferably 1–3 mole equivalents, both per mole of p-hydroxybenzaldehyde. The reaction temperature may range from 0° C. to the boiling point of the solvent or so, preferably from 0° C. to 80° C. The reaction time may range from 0.5 to 48 hours, preferably from 1 to 12 hours.

The compound of the formula (4) available by the above reaction can be used in Step 2 with or without isolation.
(Step 2)

The compound represented by the formula (6) can be obtained by reacting the compound represented by the formula (4) with a known compound represented by the formula (5) in the presence of lithium bromide and tri-n-butylphosphine oxide. This reaction is usually conducted in a suitable solvent. No particular limitation is imposed on the solvent insofar as it takes no part in the reaction. Examples of the solvent include aromatic hydrocarbons such as benzene, toluene and xylene; ethers such as diethyl ether, tetrahydrofuran and dioxane; halogenated hydrocarbons such as dichloromethane and chloroform; alkylketones such as acetone, methyl ethyl ketone and methyl isobutyl ketone; aprotic polar solvents such as N,N-dimethylformamide, N,N-dimethylacetamide, acetonitrile and dimethyl sulfoxide. Upon reaction, the compound of the formula (5) may be used in an amount of 1–1.5 mole equivalents and lithium bromide and tri-n-butylphosphine oxide in an amount of 0.01–0.3 mole equivalent, preferably 0.03–0.05 mole equivalent, both per mole of the compound of the formula (4). The reaction temperature may range from 0° C. to the boiling point of the solvent or so, preferably from 70° C. to 140° C. The reaction time may range from 0.1 to 6 hours, preferably from 0.5 to 2 hours.

The compound of the formula (6) available by the above reaction can be used in Step 3 with or without isolation.
(Step 3)

The compound represented by the formula (1-a) can be prepared by reacting the compound represented by the formula (6) with thiazolidinedione (7) in the presence of a basic compound.

It is preferred to conduct the reaction in a suitable solvent. No particular limitation is imposed on such a solvent insofar as the solvent takes no part in the reaction. Examples of the solvent include aromatic hydrocarbons such as benzene, toluene and xylene; fatty acids such as formic acid, acetic acid and propionic acid; ethers such as diethyl ether, tetrahydrofuran, dioxane and dimethoxyethane; alcohols such as methanol, ethanol, propanol, 2-propanol and butanol; aprotic polar solvents such as N,N-dimethylformamide, N,N-dimethylacetamide, acetonitrile, dimethyl sulfoxide and hexamethylphosphoric triamide.

Illustrative examples of the basic compound include organic, basic compounds such as fatty acid salts of an alkali metal, e.g., sodium acetate and potassium acetate and tertiary amines, e.g., triethylamine and pyridine; and inorganic, basic compound such as alkali metal carbonates, e.g., sodium carbonate and potassium carbonate, alkali metal bicarbonates, e.g., sodium bicarbonate and potassium bicarbonate; alkali metals, e.g., sodium and potassium, and alkali metal hydrides, e.g., sodium hydride. Upon reaction, thiazolidinedione (7) may be used in an amount of 1–3 mole equivalents and the basic compound in an amount of 0.1–5 mole equivalents, preferably 1–3 mole equivalents, both per mole of the compound of the formula (6). The reaction temperature may range from 0° C. to the boiling point of the solvent or so, preferably from 60° C. to 140° C. The reaction time may range from 0.5 to 48 hours, preferably from 1 to 12 hours.

Although the compound per se of the formula (1-a) available by the above reaction has blood-sugar lowering action, it can be used as an intermediate material in Step 4 with or without isolation.
(Step 4)

The compound represented by the formula (1-b) can be prepared by subjecting the compound represented by the formula (1-a) to catalytic reduction in the presence of a catalyst.

It is desired to conduct the reaction in a solvent. No particular limitation is imposed on such a solvent insofar as the solvent takes no part in the reaction. Examples of the solvent include ethyl acetate, methanol, tetrahydrofuran, dioxane, N,N-dimethylformamide and acetic acid. They can be used either singly or in combination. The illustrative catalysts may include palladium carbon and platinum. Hydrogen pressure may range from normal pressure to 500 atm., preferably from normal pressure to 80 atm. The reaction temperature may range from 0° C. to 100° C., preferably from room temperature to 70° C. The reaction time may range from 0.5 to 48 hours, preferably from 2 to 24 hours.

Incidentally, according to above-described Method A, optically-active thiazolidine derivatives of the present invention represented by the formula (1) can each be prepared using an optically-active compound (3).
Process B:

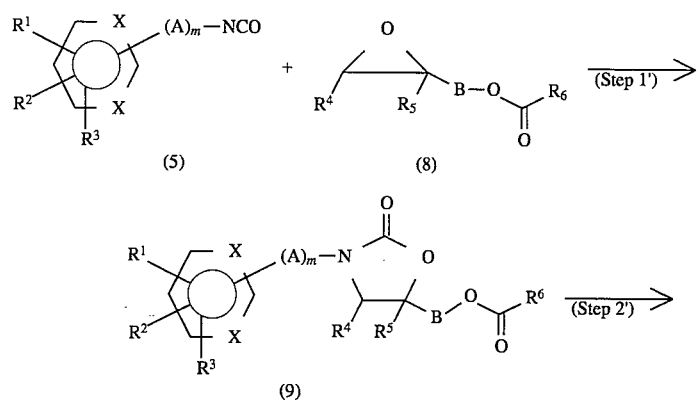

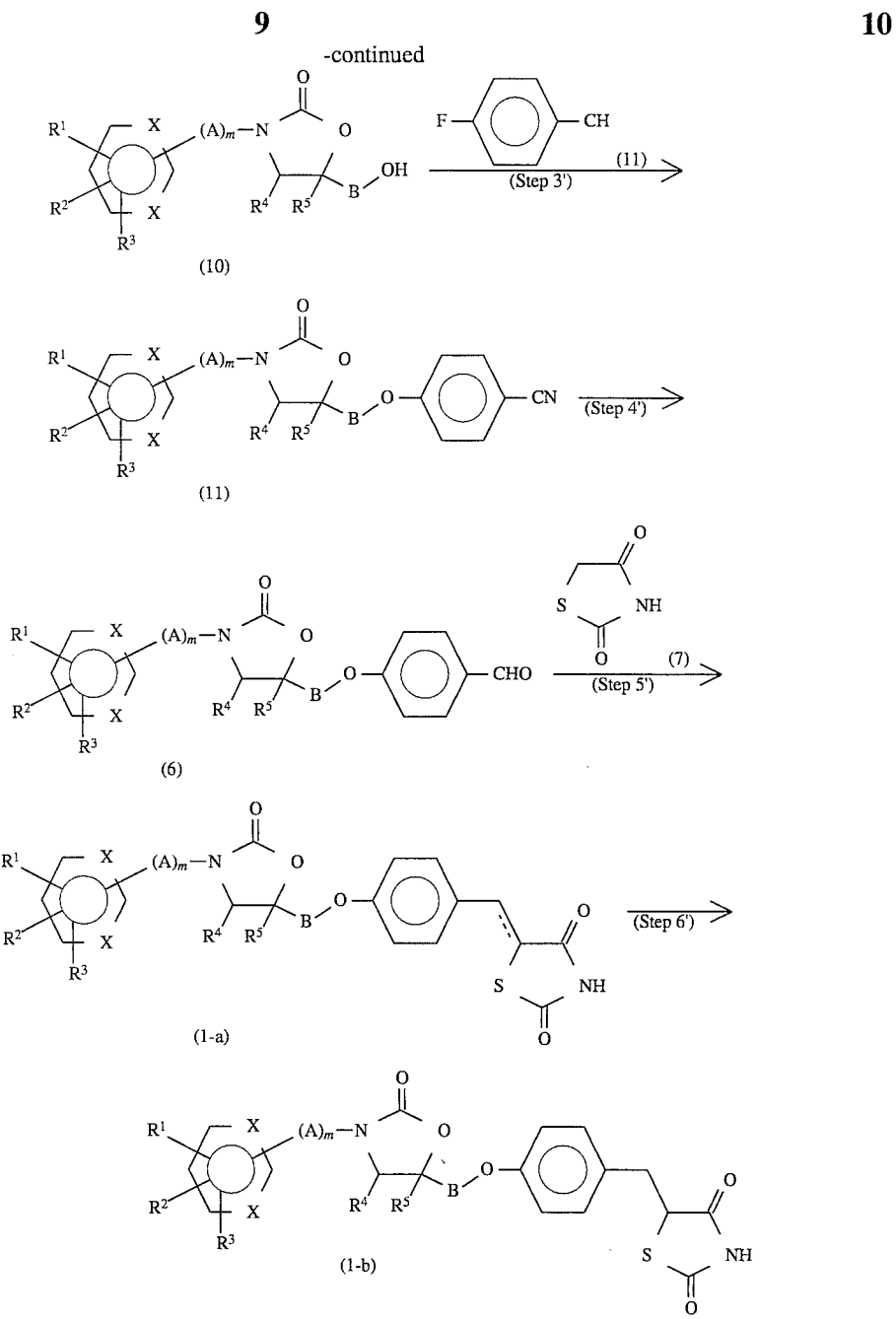

wherein $R^6$ represents a substituted or unsubstituted lower alkyl group or substituted or unsubstituted aryl group and $R^1$, $R^2$, $R^3$, $R^4$, $R^5$, A, B, X and m have the same meanings as defined above.

In the compound of the formula (8), examples of the substituted or unsubstituted lower alkyl group represented by $R^6$ include $C_{1-6}$ alkyl groups, which may be substituted by one or more halogen atom(s), such as methyl, ethyl, propyl and trifluoromethyl, while those of the substituted or unsubstituted aryl group include aryl groups, which may be substituted by one or more $C_{1-6}$ alkyl group(s), halogen atom(s) and/or nitro group(s), such as phenyl, tolyl, p-chlorophenyl and p-nitrophenyl.

The above steps 1'–4' can be conducted as follows:
(Step 1')

The compound represented by the formula (9) can be obtained by reacting a known compound represented by the formula (5) with a known compound represented by the formula (8) in the presence of lithium bromide and tri-n-butylphosphine oxide. This reaction may generally be conducted in a suitable solvent. No particular limitation is imposed on the solvent insofar as it takes no part in the reaction. Examples of the solvent include aromatic hydrocarbons such as benzene, toluene and xylene; ethers such as diethyl ether, tetrahydrofuran and dioxane; halogenated hydrocarbons such as dichloromethane and chloroform; alkylketones such as acetone, methyl ethyl ketone and methyl isobutyl ketone; aprotic polar solvents such as N,N-dimethylformamide, N,N-dimethylacetamide, acetonitrile and dimethyl sulfoxide. Upon reaction, the compound of the formula (5) may be used in an amount of 1–1.5 mole equivalents and lithium bromide and tri-n-butylphosphine oxide in an amount of 0.01–0.3 mole equivalent, preferably 0.03–0.05 mole equivalent, both per mole of the compound of the formula (8). The reaction temperature may range from 0° C. to the boiling point of the solvent or so, preferably from 70° C. to 140° C. The reaction time may range from 0.1 to 6 hours, preferably from 0.5 to 2 hours.

The compound of the formula (9) available by the above reaction can be used in Step 2' with or without isolation.
(Step 2')

The compound represented by the formula (10) can be prepared by causing an acid or basic compound to act on the compound represented by the formula (9) in a suitable inert solvent to hydrolyze the latter in a manner known per se in the art.

No particular limitation is imposed on the solvent insofar as the solvent takes no part in the reaction. Examples of the solvent include ethers such as diethyl ether, tetrahydrofuran, dioxane and anisole; halogenated hydrocarbons such as dichloromethane and chloroform; aromatic hydrocarbons such as benzene, toluene and xylene; amines such as pyridine, piperidine and triethylamine; aliphatic hydrocarbons such as hexane, heptane and octane; alkylketones such as acetone, methyl ethyl ketone and methyl isobutyl ketone; alcohols such as methanol, ethanol and propanol; acetate esters such as methyl acetate and ethyl acetate; aprotic polar solvents such as N,N-dimethylformamide, N,N-dimethylacetamide, acetonitrile, dimethyl sulfoxide and hexamethylphosphoric triamide; carbon disulfide; acetic acid; water; and mixed solvents of the above-exemplified various organic solvents with water.

Exemplary acid compounds include Lewis acids such as anhydrous aluminum chloride, stannic chloride, titanium tetrachloride, boron trichloride, boron trifluoride-ethyl ether complex and zinc chloride; inorganic acids such as hydrochloric acid, nitric acid and sulfuric acid; organic acids such as trichloro-acetic acid, trifluoroacetic acid, methanesulfonic acid and acetic acid; and acid-type ion exchange resins.

Examples of the basic compound include organic, basic compounds such as tertiary amines, e.g., triethylamine and pyridine; and inorganic, basic compound such as alkali metal carbonates, e.g., sodium carbonate and potassium carbonate, alkali metal bicarbonates, e.g., sodium bicarbonate and potassium bicarbonate; alkali metal hydroxides such as sodium hydroxide and potassium hydroxide; alkali metals, e.g., sodium and potassium, and alkali metal hydrides, e.g., sodium hydride. Upon reaction, the acid or basic compound may be used in an amount of 1–100 mole equivalents, preferably 1–20 mole equivalents per mole of the compound of the formula (9). The reaction temperature may range from −20° C. to the boiling point of the solvent or so, preferably from −10° C. to 120° C. The reaction time may range from 0.5 to 48 hours, preferably from 1 to 24 hours.

The compound of the formula (10) available by the above reaction can be used in Step 3' with or without isolation.
(Step 3')

The compound represented by the formula (12) can be prepared by reacting p-fluorobenzonitrile (11) with the compound represented by the formula (10) in a suitable solvent in the presence of a basic compound.

No particular limitation is imposed on the solvent insofar as the solvent takes no part in the reaction. Examples of the solvent include ethers such as diethyl ether, tetrahydrofuran and dioxane; halogenated hydrocarbons such as dichloromethane and chloroform; amines such as pyridine, piperidine and triethylamine; alkylketones such as acetone, methyl ethyl ketone and methyl isobutyl ketone; alcohols such as methanol, ethanol and propanol; aprotic polar solvents such as N,N-dimethylformamide, N,N-dimethylacetamide, acetonitrile, dimethyl sulfoxide and hexamethylphosphoric triamide.

Examples of the basic compound include organic, basic compounds such as tertiary amines, e.g., triethylamine and pyridine; and inorganic, basic compound such as alkali metal carbonates, e.g., sodium carbonate and potassium carbonate, alkali metal bicarbonates, e.g., sodium bicarbonate and potassium bicarbonate; alkali metal hydroxides, e.g., sodium hydroxide and potassium hydroxide; alkali metals, e.g., sodium and potassium, and alkali metal hydrides, e.g., sodium hydride. Upon reaction, p-fluorobenzonitrile (11) may be used in an amount of 1–2 mole equivalents and the basic compound in an amount of 1–5 mole equivalents, preferably 1–2 mole equivalents, both per mole of the compound of the formula (10). The reaction temperature may range from 0° C. to the boiling point of the solvent or so, preferably from 0° C. to 80° C. The reaction time may range from 0.5 to 48 hours, preferably from 1 to 8 hours.

The compound of the formula (12) available by the above reaction can be used in Step 4' with or without 10 isolation.
(Step 4')

The compound represented by the formula (6) can be obtained by causing Raney nickel to act on the compound represented by the formula (12) in a suitable inert solvent.

No particular limitation is imposed on the solvent insofar as it takes no part in the reaction. Examples of the solvent include formic acid, acetic acid, water and mixed solvents of these organic solvents with water.

Upon reaction, Raney nickel may be used in an amount of 0.5–10 grams, preferably 1–3 grams per gram of the compound of the formula (12). The reaction temperature may range from 0° C. to the boiling point of the solvent or so, preferably from 50° C. to 100° C. The reaction time may range from 0.5 to 12 hours, preferably from 1 to 3 hours.

The compound of the formula (6) available by the above reaction can be used in the following steps with or without isolation.

As shown in Steps 5' and 6' the compounds represented by the formula (1-a) and (1-b) can be prepared in accordance with Steps 3 and 4 in Process A.

Incidentally, optically-active thiazolidine derivatives of the present invention represented by the formula (1) can be prepared[ employing an optically-active compound (8).
Process C:

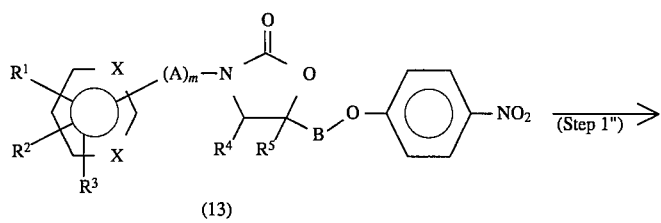

-continued

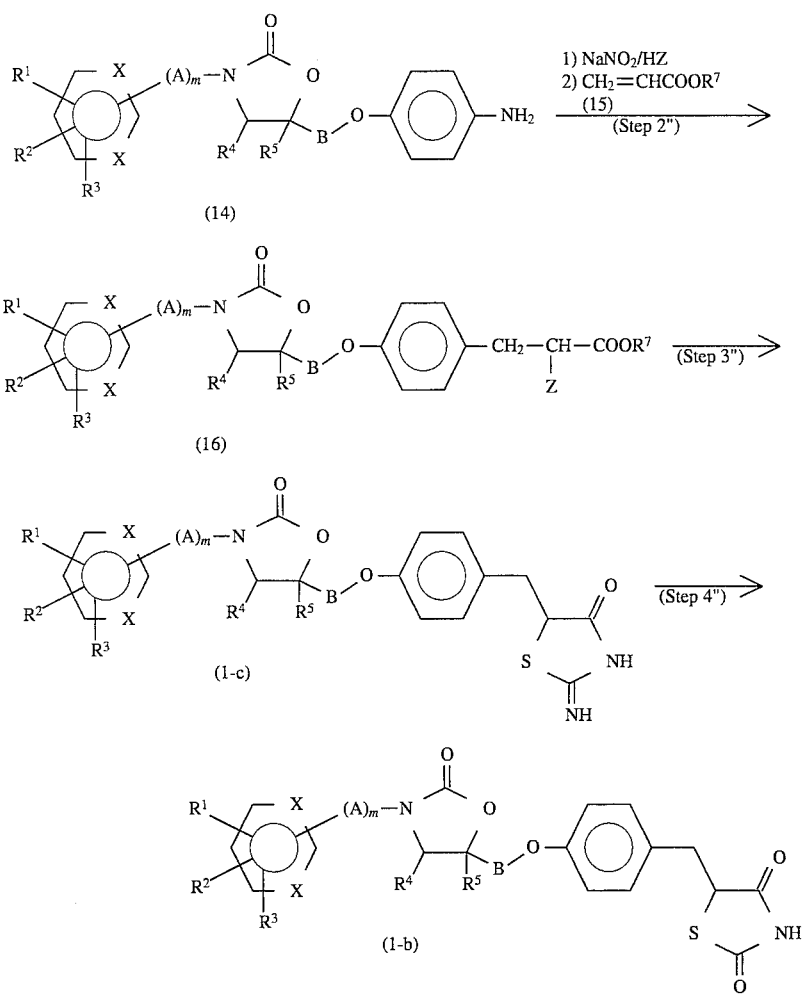

wherein R⁷ represents a lower alkyl group, Z represents a halogen atom and $R^1$, $R^2$, $R^3$, $R^4$, $R^5$, A, B, X and m have the same meanings as defined above.

In the compound of the formula (15), examples of the lower alkyl group represented by $R^7$ include linear or branched $C_{1-6}$ alkyl groups such as methyl, ethyl, n-propyl, isopropyl, n-butyl, isobutyl, sec-butyl, tertbutyl, pentyl and hexyl.

The above steps 1" to 4" can be conducted as follows:
(Step 1")

The compounds represented by the formula (14), which include novel compounds, can each be prepared usually by subjecting a known compound [Journal of Synthetic Organic Chemistry, Japan, 24, 60(1966)] represented by the formula (13) to catalytic reduction in an inert solvent in the presence of a catalyst.

No particular limitation is imposed on the solvent insofar as it takes no part in the reaction. Illustrative solvents include ethyl acetate, methanol, tetrahydrofuran, dioxane, N,N-dimethylformamide and acetic acid. They can be used either singly or in combination. Examples of the catalyst include palladium carbon and platinum. The hydrogen pressure may range from normal pressure to 500 atm., preferably from normal pressure to 80 atm. The reaction temperature may range from 0° C. to 100° C., preferably from room temperature to 70° C. The reaction time may range from 0.5 to 48 hours, preferably from 2 to 24 hours.

The compound of the formula (14) available by the above reaction can be used in Step 2" with or without isolation.
(Step 2")

The compound represented by the formula (16) can be prepared by diazotizing the compound represented by the formula (14) with sodium nitrite in a suitable solvent in the presence of hydrogen halide (HZ) and then reacting the diazotized compound with an acrylate ester (15) in the presence of cuprous oxide.

No particular limitation is imposed on the solvent insofar as it takes no part in the reaction. Examples of the solvent include ethers such as diethyl ether, tetrahydrofuran and dioxane; alkylketones such as acetone, methyl ethyl ketone and methyl isobutyl ketone; alcohols such as methanol, ethanol and propanol; aprotic polar solvents such as N,N-dimethylformamide, N,N-dimethylacetamide, acetonitrile, dimethyl sulfoxide and hexamethylphosphoric triamide; water; and acetic acid. They can be used either singly or in combination.

Upon reaction, hydrogen halide (HZ) may be used in an amount of 1–50 mole equivalents, sodium nitrite in an amount of 1–2 mole equivalents, an acrylate ester (15) in an amount of 1–10 mole equivalents and cuprous oxide in an amount of 0.05–0.5 mole equivalent, each per mole of the compound of the formula (14). The reaction temperature may range from 0° C. to the boiling point of the solvent or so, preferably from 0° C. to 50° C. The reaction time may range from 0.1 to 24 hours, preferably from 0.5 to 3 hours.

The compound of the formula (16) available by the above reaction can be used as an intermediate material in Step 3" with or without isolation.

(Step 3")

The compound represented by the formula (1-c) can be prepared by reacting the compound represented by the formula (16) with thiourea in the presence of sodium acetate.

No particular limitation is imposed on the solvent insofar as it takes no part in the reaction. Examples of the solvent include ethers such as diethyl ether, tetrahydrofuran and dioxane; alkylketones such as acetone, methyl ethyl ketone and methyl isobutyl ketone; alcohols such as methanol, ethanol and propanol; aprotic polar solvents such as N,N-dimethylformamide, N,N-dimethylacetamide, acetonitrile, dimethyl sulfoxide and hexamethylphosphoric triamide; water; and acetic acid. They can be used either singly or in combination.

Upon reaction, sodium acetate may be used in an amount of 1–3 mole equivalents and thiourea in an amount of 1–3 mole equivalents, both per mole of the compound of the formula (16). The reaction temperature may range from 0° C. to the boiling point of the solvent or so, preferably from 0° C. to 100° C. The reaction time may range from 0.5 to 24 hours, preferably from 1 to 12 hours.

Although the compound per se of the formula (1-c) available by the above reaction has blood-sugar lowering action, it can be used in Step 4" with or without isolation.

(Step 4")

The compound represented by the formula (1-b) can be prepared by causing an acid compound to act on the compound represented by the formula (1-c) to hydrolyze the latter.

It is desired that the reaction be conducted in a suitable solvent. No particular limitation is imposed on the solvent insofar as it takes no part in the reaction. Examples of the solvent include ethers such as diethyl ether, tetrahydrofuran and dioxane; alkylketones such as acetone, methyl ethyl ketone and methyl isobutyl ketone; alcohols such as methanol, ethanol and propanol; aprotic polar solvents such as N,N-dimethylformamide, N,N-dimethylacetamide, acetonitrile, dimethyl sulfoxide and hexamethylphosphoric triamide; water; acetic acid; and formic acid. They can be used either singly or in combination. Illustrative acid compounds include inorganic acids such as hydrochloric acid, nitric acid and sulfuric acid; and organic acids such as trichloroacetic acid, trifluoroacetic acid, methanesulfonic acid and acetic acid.

Upon reaction, the acid compound may be used in an amount of 1–100 mole equivalents, preferably 1–20 mole equivalents per mole of the compound of the formula (1-c). The reaction temperature may range from 0° C. to the boiling point of the solvent or so, preferably from 0° C. to 100° C. The reaction time may range from 0.5 to 60 hours, preferably from 1 to 36 hours.

Incidentally, optically-active thiazolidine derivatives of the present invention represented by the formula (1) can each be prepared employing an optically-active compound (13).

Salts of the compound (1) according to the present invention can be prepared easily by reacting the free compound of the formula (1) with the above-described acid or basic compound by a commonly-employed method.

The invention compound (1) prepared according to Process A, B or C can be isolated and purified by a common separating and purifying method such as column chromatography, recrystallization or distillation under reduced pressure.

As pharmacological dosage forms usable for administration of the compound of this invention as a pharmaceutical composition, may be mentioned oral preparations, injections, suppositories, ointments and plasters. These dosage forms can each be formulated in a manner known per se by those skilled in the art.

For the formulation of an orally-dosable solid preparation, the invention compound may be added with an excipient and optionally with a binder, disintegrator, lubricant, colorant, taste corrigent and/or smell corrigent and the resulting mixture can then be formed into tablets, coated tablets, granules, powder or capsules in a manner known per se in the art. As such additives, those commonly employed in this field can be used. Examples of the excipient include lactose, sucrose, sodium chloride, glucose, starch, calcium carbonate, kaolin, fine crystalline cellulose and silicic acid; those of the binder include water, ethanol, propanol, simple syrup, sucrose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; those of the disintegrator include dried starch, sodium alginate, agar powder, sodium bicarbonate, calcium carbonate, sodium laurylsulfate, stearic monoglyceride and lactose; those of the lubricant include purified talc, stearates, sodium borate and polyethylene glycol; and those of the taste corrigent include sucrose, bitter orange peel, citric acid and tartaric acid.

For the formulation of an orally-dosable liquid preparation, the invention compound may be added with a taste corrigent, buffer, stabilizer, smell corrigent and/or the like and then the resulting mixture can be formed into mixtures for internal use, syrups or elixirs in a manner known per se in the art. The taste corrigents exemplified above can also be used for liquid preparations. Examples of the buffer include sodium citrate and those of the stabilizer include tragacanth, acacia and gelatin.

For the formulation of an injection, the invention compound may be added with a pH adjuster, buffer, stabilizer, tonicity agent, local anesthetic and/or the like and then the resulting mixture can be formed into a subcutaneous injection, intramuscular injection or intravenous injection. Illustrative pH adjusters and buffers include sodium citrate, sodium acetate and sodium phosphate. Examples of the stabilizer include sodium pyrosulfite, EDTA, thioglycollic acid and thiolactic acid. Exemplary local anesthetics include procaine hydrochloride and lidocaine hydrochloride. Examples of the tonicity agent include sodium chloride and glucose.

For the formulation of suppositories, the invention compound may be added with a pharmaceutically-acceptable carrier which is known per se in the art such as polyethylene glycol, lanolin, cacao butter or fatty triglyceride and optionally with a surfactant such as Tween (registered trade mark) and then the resulting mixture may be formed into suppositories in a manner known per se in the art.

For the formulation of an ointment, the invention compound may be added with a base, a stabilizer, a humectant, preservatives and/or the like, which are generally employed for an ointment, as needed and they are mixed and formed into an ointment in a manner known per se in the art. Examples of the base include liquid paraffin, white petrolatum, white beeswax, octyldodecyl alcohol and paraffin; and those of the preservatives include methyl paraoxybenzoate, ethyl paraoxybenzoate and propyl paraoxybenzoate.

For the formulation of a plaster, the above-described ointment, cream, gel or paste may be coated on a usually-employed backing material. Suitable examples of the backing material include woven fabrics of cotton, rayon or chemical fibers, nonwoven fabrics and films or foamed sheets of soft PVC, polyethylene or polyurethane.

The amount of the invention compound to be incorporated in each of the above-described dosage forms varies depending on the conditions of the patient or the dosage form. In general, it is desired to incorporate the invention compound in an amount of about 1–1000 mg in an orally-dosable preparation, about 0.1–500 mg in an injection and about 5–1000 mg in a suppository. The daily dose of the pharmaceutical in the above dosage form varies depending on the conditions, body weight, age and sex of the patient and cannot be determined in any wholesale manner. In general, the daily dose may be about 0.1–5000 mg, preferably, about 1–1000 mg per adult. It is desired to conduct administration once or in 2–4 portions a day.

EXAMPLES

The present invention will hereinafter be described specifically by Referential Examples and Examples. It is, however, to be borne in mind that the present invention is by no means limited to or by them.

(1) Synthesis of compounds of the formula (6)

(Synthesis by Method A)

Referential Example 1

Synthesis of
(R)-(–)-4-(oxylanilmethoxy)-benzaldehyde [1]

In 800 ml of anhydrous methyl ethyl ketone, 23.54 g of 4-hydroxybenzaldehyde and 50 g of (R)-(–)-glycidyl m-nitrobenzenesulfonate were dissolved. To the resulting solution, 34.6 g of anhydrous potassium carbonate were added, followed by heating under reflux for 2.5 hours. The reaction mixture was filtered and the filtrate was then concentrated under reduced pressure. The residue so obtained was extracted with ethyl acetate. The extract was washed with water, dried over magnesium sulfate and then,, filtered. The filtrate was concentrated under reduced pressure. The residue was purified by subjecting same to chromatography on a silica gel column using gradient elution with hexane-ethyl acetate, whereby 30.6 g of the title compound were obtained (yield: 89%).

Specific rotation: $[\alpha]_D^{25} = -5.83°$ (c=1.0, CHCl$_3$)
Mass spectrum (EI) m/z 178 (M$^+$)

Referential Example 2

Synthesis of
(S)-(+)-4-(oxylanilmethoxy)-benzaldehyde [2]

In a similar manner to Referential Example 1 except for the use of (S)-(+)-glycidyl m-nitrobenzenesulfonate instead of (R)-(–)-glycidyl m-nitrobenzenesulfonate, the title compound was obtained in a yield of 91%.

Specific rotation: $[\alpha]_D^{25} = 6.65°$ (c=1.0, CHCl$_3$)
Mass spectrum (EI) m/z 178(M$^+$)

Referential Example 3

Synthesis of 4-(oxylanilethoxy)-benzaldehyde [3]

In a similar manner to Referential Example 1 except for the use of oxylanilethyl methanesulfonate instead of (R)-(–)-glycidyl m-nitrobenzenesulfonate, the title compound was obtained in the form of an oil in a yield of 78%.

Mass spectrum (FAB) m/z 193(M$^+$+1)

The chemical formulas of Compounds [1]–[3] and their data such as physical properties are shown in Table 1.

TABLE 1

H₂C—CH—B—O—⟨C₆H₄⟩—CHO (with epoxide O)

| Comp'd. No. | B | Melting point (°C.) | Yield (%) | $^1$H-NMR (CDCl$_3$) δ: |
|---|---|---|---|---|
| 1 | CH$_2$ (R) | 32 | 89 | 2.79(1H, dd), 2.94(1H, dd), 3.39(1H, m), 4.02(1H, dd), 4.35(1H, dd), 7.03(2H, d), 7.85(2H, d), 9.93(1H, s) |
| 2 | CH$_2$ (S) | 32 | 91 | 2.79(1H, dd), 2.94(1H, dd), 3.39(1H, m), 4.02(1H, dd), 4.35(1H, dd), 7.03(2H, d), 7.85(2H, d), 9.93(1H, s) |
| 3 | CH$_2$CH$_2$ | Oil | 78 | 1.95(1H, m), 2.20(1H, m), 2.60(1H, dd), 2.85(1H, dd), 3.16(1H, m), 4.20(2H, m), 7.01(2H, d), 7.84(2H, d), 9.89(1H, s) |

Referential Example 4

Synthesis of
4-[3-(4-methoxyphenyl)-2-oxo-oxazolidine-5-yl]methoxybenzaldehyde [4]

To a solution of 52 mg of lithium bromide and 109 mg of tri-n-butylphosphinoxide in 1 ml of xylene, a solution of 1.3 ml of 4-methoxyphenyl isocyanate and 1.78 g of 4-(oxylanilmethoxy)benzaldehyde in 5 ml of xylene was added dropwise at 140° C., followed by stirring for 2 hours at the same temperature. The reaction mixture was concentrated under reduced pressure. Ethanol was added to the residue and crystals so precipitated were collected by filtration, whereby 2.98 g of the title compound were obtained (yield: 91%). The chemical formula of the compound and its data such as physical properties are shown in Table 2.

$^1$H-NMR spectrum (CDCl$_3$) δ:
3.81(3H,s) ,4.03(1H,dd,J=8.9,5.9 Hz),
4.21(1H,t,J=8.9 Hz) ,
4.29(1H,dd,J=10.2,4.3 Hz) ,
4.33(1H,dd,J=10.2,4.6 Hz), 5.01(1H,m),
6.93(2H,d,J=9.2 Hz) , 7.03(2H,d,J=8.8 Hz) ,
7.46(2H,d,J=9.2Hz), 7.86(2H,d,J=8.8 Hz),
9.91(1H,s) .

Referential Example 5

In a similar manner to Referential Example 4 except for the substitution of the starting material by suitable ones, Compound [5]–[37], [39]–[43], [45]–[58] and [60]–[75] were synthesized, respectively. The chemical formulas of the compounds and their data such as physical properties are shown in Tables 2–12.

TABLE 2
![structure with R1, R2, R3 on phenyl, N-C(=O)-O-CH(CH2)-CH2-O-C6H4-CHO]
| Comp'd. No. | R¹ | R² | R³ | Melting point (°C.) | Yield (%) | Elemental analysis (%) Calculated (Found) C | H | N |
|---|---|---|---|---|---|---|---|---|
| 4 | 4-OMe | H | H | 135–137 | 91 | 66.05 (66.23 | 5.23 5.36 | 4.28 4.40) |
| 5 | 3-OMe | H | H | 177–179 | 86 | 66.05 (66.24 | 5.23 5.03 | 4.27 4.32) |
| 6 | 2-OMe | H | H | 93–95 | 42 | 66.05 (65.90 | 5.23 4.94 | 4.27 4.33) |
| 7 | 2-OMe | 4-OMe | H | 137–139 | 85 | 63.86 (63.48 | 5.36 5.48 | 3.92 3.81) |
| 8 | 4-OEt | H | H | 132–134 | 85 | 66.85 (65.94 | 5.61 5.75 | 4.10 4.12) |
| 9 | 2-OEt | H | H | Oil | 92 | 60.78 (60.66 | 4.88 4.89 | 6.16 6.04) |
| 10 | 4-Cl | H | H | 113–115 | 69 | 61.55 (61.52 | 4.25 4.25 | 4.22 4.26) |
| 11 | 2-F | 4-Br | H | 130–133 | 87 | 51.80 (51.78 | 3.32 3.34 | 3.55 3.61) |
| 12 | 4-F | H | H | 161–164 | 75 | 64.76 (64.72 | 4.48 4.44 | 4.44 4.41) |
| 13 | 2-F | 4-F | H | 129–131 | 79 | 61.26 (61.29 | 3.93 4.07 | 4.20 4.20) |
| 14 | 2-F | 4-F | 6-F | 115–116 | 53 | 58.13 (58.10 | 3.44 3.46 | 3.99 3.93) |
| 15 | 3-F | 4-F | H | 141–143 | 67 | 61.26 (61.31 | 3.93 3.97 | 4.20 4.15) |
TABLE 3
| Comp'd. No. | R¹ | R² | R³ | Melting point (°C.) | Yield (%) | Elemental analysis (%) Calculated (Found) C | H | N |
|---|---|---|---|---|---|---|---|---|
| 16 | 2-Cl | 4-Cl | H | 111–113 | 37 | 55.76 (55.74 | 3.58 3.51 | 3.82 3.86) |
| 17 | 3-Cl | 4-Cl | H | 136–139 | 83 | 55.76 (55.81 | 3.58 3.69 | 3.82 3.84) |
| 18 | 3-F | H | H | 159–161 | 86 | 64.76 (64.90 | 4.48 4.48 | 4.44 4.41) |
| 19 | 2-Cl | H | H | 92–93 | 46 | 61.55 (61.58 | 4.25 4.17 | 4.22 4.22) |
| 20 | 2-F | 4-Cl | H | 129–131 | 70 | 58.38 (58.38 | 3.75 3.71 | 4.00 4.09) |
| 21 | 4-COOEt | H | H | 151–152 | 79 | 65.03 (65.12 | 5.18 5.22 | 3.79 3.81) |
| 22 | H | H | H | 168–169 | 81 | 68.68 (68.69 | 5.09 5.13 | 4.71 4.63) |
| 23 | 4-Me | H | H | 158–160 | 86 | 69.44 (69.66 | 5.50 5.73 | 4.50 4.59) |
| 24 | 4-Et | H | H | 120–122 | 78 | 70.14 (70.40 | 5.88 5.91 | 4.31 4.37) |
| 25 | 4-iso-Pr | H | H | 131–134 | 84 | 70.78 (70.73 | 6.24 6.20 | 4.13 4.11) |
| 26 | 3,4- ⌒ | | H | 140–142 | 94 | 71.20 (71.18 | 5.68 5.71 | 4.15 4.18) |

TABLE 3-continued
| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 27 | 4-NMe₂ | H | H | 183–185 | 70 | 67.05 (67.18 | 5.92 6.00 | 8.23 8.24) |
| 28 | 4-O–⟨ | H | H | 122–124 | 78 | 67.60 (67.75 | 5.95 6.01 | 3.94 4.01) |
TABLE 4
| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 29 | 4-OCF₃ | H | H | 96–98 | 33 | 56.70 (56.97 | 3.70 3.72 | 3.67 3.69) |
| 30 | 4-CF₃ | H | H | 129–130 | 85 | 59.18 (59.03 | 3.86 3.93 | 3.83 3.81) |
| 31 | 3-CF₃ | H | H | 119–120 | 58 | 59.18 (59.35 | 3.86 3.93 | 3.83 3.77) |
| 32 | 2-CF₃ | H | H | 64–66 (·⅓H₂O) | 64 | 58.23 (58.23 | 3.98 3.86 | 3.77 3.79) |
TABLE 5
| Comp'd. No. | R¹ | R² | R³ | Melting point (°C.) | Yield (%) | Elemental analysis (%) or ¹H-NMR, Calculated (Found) (DMSO-d₆) δ: | | |
|---|---|---|---|---|---|---|---|---|
| | | | | | | C | H | N |
| 33 | 3,4- O–CH₂–O | | H | 160–162 | 88 | 63.34 (63.39 | 4.43 4.50 | 4.10 4.11) |
| 34 | 3,4- O–CH₂CH₂–O | | H | 196–197 | 88 | 64.22 (64.32 | 4.82 4.87 | 3.94 3.96) |

TABLE 5-continued

| Comp'd. No. | R¹ | R² | R³ | Melting point (°C.) | Yield (%) | Elemental analysis (%) or ¹H-NMR, Calculated (Found) (DMSO-$d_6$) δ: | | |
|---|---|---|---|---|---|---|---|---|
| | | | | | | C | H | N |
| 35 | 4-(2-methylpyrrole-N-carbonyloxy) | H | H | 230–232 | 49 | 65.93 (65.80 | 4.43 4.46 | 7.69 7.61) |
| 36 | 4-$NO_2$ | H | H | 167–169 | 99 | 59.65 (59.34 | 4.12 4.05 | 8.18 8.26) |
| 37 | 4-CN | H | H | 180–182 | 66 | 4.12(1H, dd), 4.30(1H, dd), 4.34(1H, dd), 4.42(1H, dd), 5.12(1H, m), 7.04(2H, d), 7.70(2H, d), 7.75(2H, d), 7.85(2H, d), 9.90(1H, s) | | |
| 38 | 4-CHO | H | H | 130–132 | 89 | 66.46 (66.39 | 4.65 4.70 | 4.31 4.60) |

TABLE 6

| Comp'd. No. | R¹ | R² | R⁵ | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|---|
| | | | | | | | C | H | N |
| 39 | 4-$CF_3$ | H | H | −74.45° (1.0, $CHCl_3$) | 132–133 | 68 | 59.18 (59.30 | 3.86 3.81 | 3.83 3.78) |
| 40 | 4-OMe | H | H | −78.68° (1.0, $CHCl_3$) | 105–107 | 64 | 66.05 (65.76 | 5.23 5.53 | 4.28 4.49) |
| 41 | 4-Cl | 2-F | H | −88.62° (1.0, $CHCl_3$) | 103–105 | 59 | 58.38 (58.43 | 3.75 3.58 | 4.00 4.05) |
| 42 | 4-F | 3-F | H | −69.19° (1.0, $CHCl_3$) | 108–110 | 60 | 61.26 (61.22 | 3.93 3.89 | 4.20 4.18) |
| 43 | 4-$OCF_3$ | H | H | −59.60° (1.01, $CHCl_3$) | 76–79 | 56 | 56.70 (56.62 | 3.70 3.82 | 3.67 3.65) |
| 44 | 4-OMe | H | Me | −75.79° (1.0, $CHCl_3$) | Oil (.⅓$H_2O$) | 85 | 66.16 (66.32 | 5.67 5.66 | 4.06 4.09) |

TABLE 7

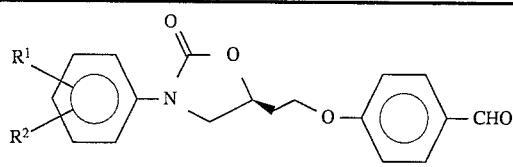

| Comp'd. No. | R¹ | R² | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|
| | | | | | | C | H | N |
| 45 | 4-CF₃ | H | −23.95° (1.01, CHCl₃) | 135–137 | 99 | 60.16 (60.13) | 4.25 4.29 | 3.69 3.73) |
| 46 | 4-OMe | H | −29.39° (1.00, CHCl₃) | 118–120 | 91 | 66.85 (66.96) | 5.61 5.63 | 4.10 4.17) |
| 47 | 4-Cl | 2-F | −39.90° (1.02, CHCl₃) | 77–78 | 71 | 59.43 (59.38) | 4.16 4.08 | 3.85 3.84) |
| 48 | 3,4- O-CH₂-O | | −24.39° (1.00, CHCl₃) | 129–131 | 93 | 64.22 (64.28) | 4.82 4.87 | 3.94 4.03) |
| 49 | 4-OEt | H | −26.47° (1.02, CHCl₃) | 124–126 | 88 | 67.59 (67.60) | 5.96 6.05 | 3.94 4.00) |
| 50 | 4-Et | H | −30.00° (1.0, CHCl₃) | 122–124 | 86 | 70.78 (70.72) | 6.24 6.44 | 4.13 4.14) |
| 51 | 4-OCF₃ | H | −12.77° (1.01, CHCl₃) | 94–96 | 71 | 57.73 (57.72) | 4.08 4.16 | 3.54 3.62) |

TABLE 8

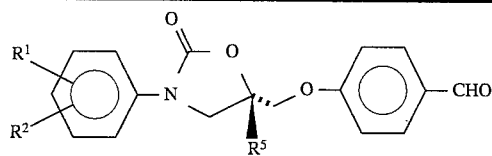

| Comp'd. No. | R¹ | R² | R⁵ | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|---|
| | | | | | | | C | H | N |
| 52 | 4-CF₃ | H | H | 76.27° (1.0, CHCl₃) | 132–133 | 75 | 59.18 (59.23) | 3.89 3.82 | 3.83 3.80) |
| 53 | 4-OMe | H | H | 77.04° (1.0, CHCl₃) | 103–105 | 79 | 66.05 (65.99) | 5.23 5.38 | 4.28 4.65) |
| 54 | 4-Cl | 2-F | H | 87.59° (1.0, CHCl₃) | 105–107 | 64 | 58.38 (58.36) | 3.75 3.59 | 4.00 4.01) |
| 55 | 4-F | 3-F | H | 63.39° (1.0, CHCl₃) | 108–109 | 50 | 61.26 (61.32) | 3.93 3.92 | 4.20 4.19) |
| 56 | 4-OEt | H | H | 73.46° (1.01, CHCl₃) | 141–143 | 96 | 66.85 (66.71) | 5.61 5.59 | 4.10 4.14) |
| 57 | 4-OCF3 | H | H | 59.20° (1.01, CHCl₃) | 63–64 | 76 | 56.70 (56.30) | 3.70 3.66 | 3.67 3.66) |
| 58 | 3,4- O-CH₂-O | | H | 55.78° (1.02, CHCl₃) | 148–150 | 94 | 63.34 (63.26) | 4.43 4.31 | 4.10 4.25) |
| 59 | 4-OME | H | Me | 72.39° (1.0, CHCl₃) | Oil (.⅓H₂O) | 85 | 66.16 (66.34) | 5.67 5.77 | 4.06 4.04) |

TABLE 9

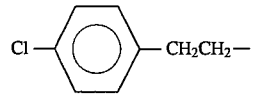

| Comp'd. No. | R¹ | R² | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|
| | | | | | | C | H | N |
| 60 | 4-CF₃ | H | 20.39° (1.01, CHCl₃) | 133–135 | 72 | 60.16 (60.02 | 4.25 4.19 | 3.69 3.76) |
| 61 | 4-OMe | H | 26.60° (1.00, CHCl₃) | 114–115 | 88 | 66.85 (66.76 | 5.61 5.56 | 4.10 4.14) |

TABLE 10

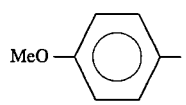

| Comp'd. No. | R | B | Melting point (°C.) | Yield (%) | Elemental analysis (%) or ¹H-NMR, Calculated (Found) (DMSO-d₆) δ: | | |
|---|---|---|---|---|---|---|---|
| | | | | | C | H | N |
| 62 | 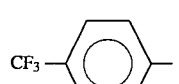 Cl—〈 〉—CH₂CH₂— | —CH₂— | 67–69 | 82 | 62.38 (62.57 | 5.14 5.11 | 3.83 3.86) |
| 63 | MeO—〈 〉— | —CH₂CH₂— | 116–117 | 57 | 66.85 (66.78 | 5.61 5.70 | 4.10 4.27) |
| 64 | CF₃—〈 〉— | —CH₂CH₂— | 129–131 | 53 | 60.16 (59.97 | 4.25 4.23 | 3.69 3.70) |
| 65 | 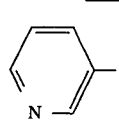 | —CH₂— | 135–137 | 27 | 4.00(1H, dd), 4.30(1H, dd), 4.40(1H, dd), 4.46(1H, dd) 5.16(1H, m), 7.17(2H, d), 7.45(1H, dd), 7.89(2H, d), 8.05(1H, ddd), 8.36(1H, dd), 8.80(1H, d), 9.89(1H, s) | | |
| 66 | 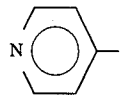 | —CH₂— | 153–155 | 58 | 3.96(1H, dd), 4.26(1H, dd), 4.40(1H, dd), 4.46(1H, dd) 5.16(1H, m), 7.16(2H, d), 7.58(1H, dd), 7.89(2H, d), 8.52(1H, dd), 9.89(1H, s) | | |
| 67 | 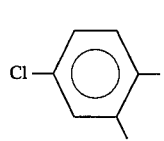 | —CH₂CH₂— | 77–78 | 83 | 59.43 (59.55 | 4.16 4.35 | 3.85 3.83) |

TABLE 10-continued
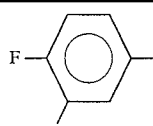
| Comp'd. No. | R | B | Melting point (°C.) | Yield (%) | Elemental analysis (%) or ¹H-NMR, Calculated (Found) (DMSO-$d_6$) δ: | | |
|---|---|---|---|---|---|---|---|
| | | | | | C | H | N |
| 68 | 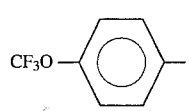 | —CH$_2$CH$_2$— | 84–86 | 73 | 62.25 (62.31 | 4.35 4.24 | 4.03 4.06) |
| 69 | 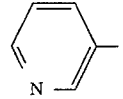 | —CH$_2$CH$_2$— | 96–98 | 71 | 57.73 (57.83 | 4.08 3.98 | 3.54 3.54) |
TABLE 11
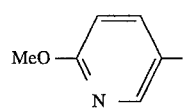
| Comp'd. No. | R | Specific rotation $[\alpha]_D^{25}$ (concentration, solvent) | Melting point (°C.) | Yield (%) | Elemental analysis (%) Calculated (Found) | | |
|---|---|---|---|---|---|---|---|
| | | | | | C | H | N |
| 70 | 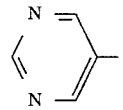 | −83.10° (1.0, CHCl$_3$) | 135–137 | 67 | 64.42 (64.33 | 4.73 4.77 | 9.39 9.38) |
| 71 | 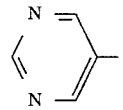 | −84.95° (1.1, CHCl$_3$) | 126–128 | 53 | 62.19 (62.14 | 4.91 4.90 | 8.53 8.33) |
| 72 | 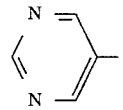 | −96.40° (0.5, CHCl$_3$) | 132–134 | Stoichiometric | 60.20 (60.01 | 4.38 4.29 | 14.04 13.95) |

TABLE 12

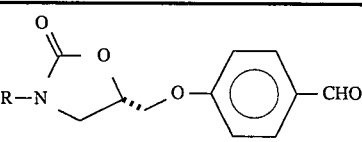

| Comp'd. No. | R | Specific rotation $[\alpha]_D^{25}$ (concentration, solvent) | Melting point (°C.) | Yield (%) | Elemental analysis (%) Calculated (Found) | | |
|---|---|---|---|---|---|---|---|
| | | | | | C | H | N |
| 73 | 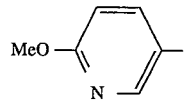 | 87.50° (1.0, CHCl$_3$) | 137–139 (.1/4H$_2$O) | 70 | 63.47 (63.43 | 4.83 4.62 | 9.25 9.26) |
| 74 | MeO-pyridyl | 87.76° (1.0, CHCl$_3$) | 126–128 | 65 | 62.19 (62.09 | 4.91 4.91 | 8.53 8.55) |
| 75 | pyrimidyl | 88.00° (0.5, CHCl$_3$) | 123–125 (.1/5H$_2$O) | 61 | 59.48 (59.42 | 4.46 4.20 | 13.87 14.17) |

(Synthesis by Method B)

Referential Example 6

Synthesis of (4S,5S)-(−)-3-(4-methoxyphenyl)-4-methyl-2-oxooxazolidin-5-ylmethyl p-nitrobenzoate [76]

The reaction was conducted in a similar manner to Referential Example 4 except that (2S,3S)-(−)-3-methyl-glycidyl p-nitrobenzoate was used instead of 4-(oxylanilmethoxy)-benzaldehyde, whereby the title compound was obtained in a yield of 75%.

Specific rotation: $[\alpha]_D^{25}=-55.39°$ (c=1.0, CHCl$_3$)
$^1$H-NMR spectrum (CDCl$_3$) δ:
1.38(3H,d,J=6.2 Hz), 3.81(3H,s), 4.23(1H,m),
4.4–4.75(3H,m), 6.92(2H,d,J=11.2 Hz),
7.27(2H,d,J=11.2 Hz), 8.19(2H,d,J=8.9 Hz),
8.28 (2H, d, J=8.9 Hz).

Referential Example 7

Synthesis of (R)-(−)-3-(4-methoxyphenyl)-5-methyl-2-oxooxazolidin-5-ylmethyl p-nitrobenzoate [77]

The reaction was conducted in a similar manner to Referential Example 4 except that (R)-(−)-2-methyl-glycidyl p-nitrobenzoate was used instead of 4-(oxylanilmethoxy)-benzaldehyde, whereby the title compound was obtained in a yield of 92%.

Specific rotation: $[\alpha]_D^{25}=-71.28°$ (c=1.0, CHCl$_3$)
$^1$H-NMR spectrum (CDCl$_3$) δ:
1.60(3H,s), 3.74(3H,s), 3.94 (1H,d,J=9.4 Hz),
4.10(1H,d,J=9.4 Hz), 4.49(1H,d,J=11.8 Hz),
4.54(1H,d,J=11.8 Hz), 6.97 (2H,d,J=9.2 Hz),
7.46(2H,d,J=9.2 Hz), 8.12 (2H,d,J=8.9 Hz),
8.30(2H,d,J=8.9 Hz).

Referential Example 8

Synthesis of (S)-(+)-3-(4-methoxyphenyl)-5-methyl-2-oxooxazolidin-5-ylmethyl p-nitrobenzoate [78]

The reaction was conducted in a similar manner to Referential Example 4 except that (S)-(+)-2-methyl-glycidyl p-nitrobenzoate was used instead of 4-(oxylanilmethoxy)-benzaldehyde, whereby the title compound was obtained in a yield of 96%.

Specific rotation: $[\alpha]_D^{25}=71.79°$ (c=1.0, CHCl$_3$)
$^1$H-NMR spectrum (CDCl$_3$) δ:
1.60(3H,s), 3.74(3H,s), 3.94(1H,d,J=9.4 Hz),
4.10(1H,d,J=9.4 Hz), 4.49(1H,d,J=11.8 Hz),
4.54(1H,d,J=11.8 Hz), 6.97(2H,d,J=9.2 Hz),
7.46(2H,d,J=9.2 Hz), 8.12 (2H,d,J=8.9 Hz),
8.30 (2H,d,J=8.9 Hz).

The chemical formulas of Compounds [76]–[78] and their data such as physical properties are shown in Table 13.

TABLE 13

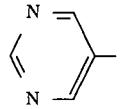

| Comp'd. No. | R$^4$ | R$^5$ | Melting point (°C.) | Yield (%) | Elemental analysis (%) Calculated (Found) | | |
|---|---|---|---|---|---|---|---|
| | | | | | C | H | N |
| 76 | CH$_3$ (S) | H (S) | 138–140 | 75 | 59.07 (59.38 | 4.70 4.73 | 7.25 7.42) |

TABLE 13-continued

[Chemical structure: CH₃O-phenyl-N(C(=O)O ring)-CHR⁴-CR⁵-CH₂-O-C(=O)-phenyl-NO₂]

| Comp'd. No. | $R^4$ | $R^5$ | Melting point (°C.) | Yield (%) | Elemental analysis (%) Calculated (Found) C | H | N |
|---|---|---|---|---|---|---|---|
| 77 | H | CH₃ (R) | 155–157 | 92 | 59.07 (59.20 | 4.07 4.78 | 7.25 7.16) |
| 78 | H | CH₃ (S) | 156–158 | 96 | 59.07 (59.28 | 4.07 4.69 | 7.25 7.22) |

Referential Example 9

Synthesis of (4S,5S)-(−)-3-(4-methoxyphenyl)-4-methyl-2-oxooxazolidin-5-ylmethylalcohol [79]

To a solution of 2.43 g of Compound [76], which had been obtained in Referential Example 6, in 20 ml of methanol, 3.8 ml of an 8% aqueous solution of sodium hydroxide were added, followed by stirring at 50° C. for 20 hours. The reaction mixture was concentrated under reduced pressure. The residue so obtained was extracted with ethyl acetate. The extract was washed with water, dried over magnesium sulfate and then filtered. The filtrate was concentrated under reduced pressure, The residue was purified by subjecting same to chromatography on a silica gel column using gradient elution with hexane-ethyl acetate, whereby 1.04 g of the title compound were obtained (yield: 70%).

Specific rotation: $[\alpha]_D^{25} = -21.19°$ (c=1.0, CHCl₃)

Referential Example 10

Synthesis of (R)-(−)-3-(4-methoxyphenyl)-5-methyl-2-oxooxazolidin-5-ylmethylalcohol [80]

The reaction was conducted in a similar manner to Referential Example 9 except that Compound [77] obtained in Referential Example 7 was used instead of Compound [76], whereby the title compound was obtained in a yield of 90%.

Specific rotation: $[\alpha]_D^{25} = -24.89°$ (c=1.0, CHCl₃)

Referential Example 11

Synthesis of (S)-(+)-3-(4-methoxyphenyl)-5-methyl-2-oxooxazolidin-5-ylmethylalcohol [81]

The reaction was conducted in a similar manner to Referential Example 9 except that Compound [78] obtained in Referential Example 8 was used instead of Compound [76], whereby the title compound was obtained in a yield of 95%.

Specific rotation: $[\alpha]_D^{25} = 21.39°$ (c=1.0, CHCl₃)

The chemical formulas of Compounds [79]–[81] and their data such as physical properties are shown in Table 14.

TABLE 14

[Chemical structure: CH₃O-phenyl-N(C(=O)O ring)-CHR⁴-CR⁵-CH₂OH]

| Comp'd. No. | $R^4$ | $R^5$ | Melting point (°C.) | Yield (%) | ¹H-NMR (CDCl₃) δ: |
|---|---|---|---|---|---|
| 79 | CH₃ (S) | H (S) | 99–101 | 70 | 1.29(3H, d), 2.13(1H, dd), 3.75(1H, ddd), 3.81(3H, s) 3.98(1H, ddd), 4.2–4.34(2H, m), 6.92(2H, d), 7.26(2H, d) |
| 80 | H | CH₃ (R) | 133–134 | 90 | 1.50(3H, s), 2.39(1H, dd), 3.58(1H, dd), 3.63(1H, d), 3.78(1H, dd), 3.80(3H, s), 4.08(1H, d), 6.89(2H, d), 7.43(2H, d) |
| 81 | H | CH₃ (S) | 131–132 | 95 | 1.50(3H, s), 2.39(1H, dd), 3.58(1H, dd), 3.63(1H, d), 3.78(1H, dd), 3.80(3H, s), 4.08(1H, d), 6.89(2H, d), 7.43(2H, d) |

Referential Example 12

Synthesis of 4-[(4S,5S)-(−)-3-(4-methoxyphenyl)-4-methyl-2-oxooxazolidin-5-yl]methoxybenzonitrile [82]

To a suspension of 200 mg of 60% sodium hydride in 1 ml of anhydrous N,N-dimethylformamide, a solution of 0.98 g of Compound [79], which had been obtained in Referential Example 9, in 7 ml of N,N-dimethylformamide was added dropwise, followed by stirring at 50° C. for 25 minutes. At the same temperature, a solution of 500 mg of p-fluorobenzonitrile in 2 ml of anhydrous N,N-dimethylformamide was added to the reaction mixture, followed by stirring for 30 minutes. The reaction mixture was concentrated under reduced pressure. The residue so obtained was extracted with ethyl acetate. The extract was washed with water, dried over magnesium sulfate and filtered. The filtrate so obtained was concentrated under reduced pressure. The residue was purified by subjecting same to chromatography on a silica gel column using gradient elution with hexane-ethyl acetate, whereby 0.98 g of the title compound was obtained (yield: 70%).

Specific rotation: $[\alpha]_D^{25} = -74.70°$ (c=1.0, CHCl₃)
¹H-NMR spectrum (CDCl₃) δ:

1.39(3H,d,J=6.3 Hz), 3.82(3H,s),
4.28(2H,d,J=4.6 Hz),
4.35(1H,dq,J=4.9,6.3 Hz),
3.5(1H, dt, J=4.9,4.6 Hz ),
6.94(2H, d, J=8.9 Hz ), 6.99(2H,d,J=8.9 Hz), 7.30(2H,d,J-8.9 Hz), 7.62(2H,d,J=8.9 Hz).

Referential Example 13

Synthesis of 4-[ (R)-(–) -3-(4-methoxyphenyl)-5-methyl-2-oxooxazolidin-5-yl]methoxybenzonitrile [83]

The reaction was conducted in a similar manner to Referential Example 12 except for the use of Compound [80] obtained in Referential Example 10 instead of the compound [79], whereby the title compound was obtained in a yield of 76%.

Specific rotation: $[\alpha]_D^{25} = -83.56°$ (c=1.0, CHCl$_3$)
$^1$H-NMR spectrum (CDCl$_3$) δ:

1.68(3H,s), 3.79(1H,d,J=8.9 Hz), 3.80(3H,s),
4.03(1H,d,J=9.6 Hz) , 4.12(1H,d,J=8.9 Hz) ,
4.17(1H,d,J=9.6 Hz), 6.92(2H,d,J=9.2 Hz) ,
6.96(2H,d,J=9.2 Hz), 7.45(2H,d,J=9.2 Hz),
7.60 (2H, d,J=9.2 Hz ).

Referential Example 14

Synthesis of 4-[(S)-(+)-3-(4-methoxyphenyl)-5-methyl-2-oxooxazolidin-5-yl]methoxybenzonitrile[84]

The reaction was conducted in a similar manner to Referential Example 12 except for the use of Compound [80] obtained in Referential Example 10 instead of Compound [79], whereby the title compound was obtained in a yield of 76%.

Specific rotation: $[\alpha]_D^{25}=73.86°$ (c=1.0, CHCl$_3$)
$^1$H-NMR spectrum (CDCl$_3$) δ:

1.68(3H,s), 3.79(1H,d,J=8.9 Hz), 3.80(3H,s),
4.03(1H,d,J=9.6 Hz), 4.12(1H,d,J=8.9 Hz),
4.17(1H,d,J=9.6 Hz), 6.92(2H,d,J=9.2 Hz),
6.96(2H,d,J=9.2 Hz) , 7.45(2H,d,J=9.2 Hz),
7.60(2H, d ,J=9.2 Hz ).

Referential Example 15

Synthesis of 4-[(4S,5S)-(–)-3-(4-methoxyphenyl)-4-methyl-2-oxooxazolidin-5-yl]methoxybenzaldehyde [85]

To a solution of 0.88 g of Compound [82], which had been obtained in Referential Example 12, dissolved in 25 ml of 80% aqueous formic acid, 1.8 g of Raney nickel were added, followed by heating under reflux for 1.5 hours. The reaction mixture was concentrated under reduced pressure. The residue so obtained was extracted with ethyl acetate. The extract was washed with aqueous sodium bicarbonate, dried over anhydrous magnesium sulfate and then filtered. The filtrate was concentrated under reduced pressure. The residue was purified by subjecting same to chromatography on a silica gel column using gradient elution with hexane-ethyl acetate, whereby 0.71 g of the title compound was obtained (yield: 80%).

Specific rotation: $[\alpha]_D^{25}=-68.99°$ (c=1.0, CHCl$_3$)
$^1$H-NMR spectrum (CDCl$_3$) δ:

1.39(3H,d,J=6.0 Hz), 3.82(3H,s),
4.31(2H,d,J=4.6 Hz),
4.37(1H,dq,J=4.9,6.3 Hz),
3.52 (1H,dt,J=4.9,4.6 Hz) ,
6.94 (2H,d,J=8.9 Hz) ,
7.04(2H,d,J=8.9 Hz), 7.31(2H,d,J=8.9 Hz),
7.87(2H,d,J=8.9 Hz), 9.92(1H,s).

The chemical formulas of Compounds [82]–[85] and their data such as physical properties are shown in Table 15.

TABLE 15

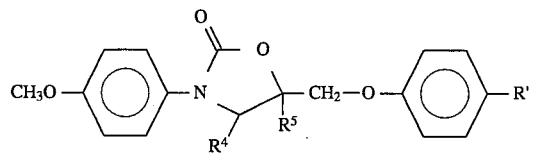

| Comp'd. | | | | Melting point | Yield | Elemental analysis (%) Calculated (Found) | | |
|---|---|---|---|---|---|---|---|---|
| No. | R$^4$ | R$^5$ | R' | (°C.) | (%) | C | H | N |
| 82 | CH$_3$ (S) | H (S) | CN | 127–128 | 70 | 67.45 (67.39) | 5.36 5.41 | 8.28 8.27) |
| 83 | H | CH$_3$ (R) | CN | 147–149 | 76 | 67.45 (67.62) | 5.36 5.38 | 8.28 8.30) |
| 84 | H | CH$_3$ (S) | CN | 146–147 | 76 | 67.45 (67.63) | 5.36 5.40 | 8.28 8.27) |
| 85 | CH$_3$ (S) | H (S) | CHO | 115–116 | 80 | 66.85 (67.02) | 5.61 5.82 | 4.10 4.30) |
| 86 | CH$_3$ (S) | H (S) | 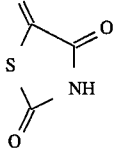 | 155–157 | 85 | 59.99 (60.10) | 4.58 4.47 | 6.36 6.16) |

TABLE 15-continued

[Structure: CH₃O—C₆H₄—N(R⁴-CH)—C(R⁵)(OC(=O)O)—CH₂—O—C₆H₄—R']

| Comp'd. No. | R⁴ | R⁵ | R' | Melting point (°C.) | Yield (%) | Elemental analysis (%) Calculated (Found) | | |
|---|---|---|---|---|---|---|---|---|
| | | | | | | C | H | N |
| 87 | CH₃ (S) | H (S) | —CH₂—CH(S)(C(=O)NH-C(=O)) | Foam | 62 | 59.72 (59.62 | 5.01 5.26 | 6.33 6.16) |

Referential Example 16

Synthesis of 4-[ (R)-(−)-3-(4-methoxyphenyl)-5-methyl-2-oxooxazolidin-5-yl]methoxybenzaldehyde [44]

The reaction was conducted in a similar manner to Referential Example 15 except for the use of Compound [83] obtained in Referential Example 13 instead of Compound [82], whereby the title compound was obtained in the form of an oil in a yield of 85%.

$^1$H-NMR spectrum (CDCl$_3$) δ:
1.69(3H,s), 3.80(1H,d,J=8.9 Hz),
3.81(3H,s), 4.07 (1H,d,J=9.6 Hz),
4.13(1H,d,J=8.9 Hz), 4.21(1H,d,J=9.6 Hz),
6.92(2H,d,J=9.2 Hz), 7.01(2H,d,J=8.9 Hz),
7.46(2H,d,J=9.2 Hz), 7.85(2H,d,J=8.9 Hz),
9.90(1H,s) .

The chemical formula of Compound [44] and its data such as physical properties are shown in Table 6.

Referential Example 17

Synthesis of 4-[(S)-(+)-3-(4-methoxyphenyl)-5-methyl-2-oxooxazolidin-5-yl]methoxybenzaldehyde [59]

The reaction was conducted in a similar manner to Referential Example 15 except for the use of Compound [84] obtained in Referential Example 14 instead of the compound [82], whereby the title compound was obtained in the form of an oil in a yield of 85%.

$^1$H-NMR spectrum (CDCl$_3$) δ:
1.69(3H,s), 3.80(1H,d,J=8.9 Hz), 3.81(3H,s),
4.07 (1H,d,J=9.6 Hz) , 4.13(1H,d,J=8.9 Hz),
4.21 (1H,d,J=9.6 Hz) , 6.92 (2H,d,J=9.2 Hz) ,
7.01 (2H,d,J=8.9 Hz) , 7.46(2H,d,J=9.2 Hz) ,
7.85(2H,d,J=8.9 Hz), 9.90(1H,s).

The chemical formula of Compound [59] and its data such as physical properties are shown in Table 8.

Referential Example 18

Synthesis of 4-[3-(formylphenyl)-2-oxooxazolidin-5-yl]methoxybenzaldehyde [38]

The reaction was conducted in a similar manner to Referential Example 15 except for the use of Compound [37] obtained in Referential Example 5, that is, 4-[3-( 4-cyanophenyl)-2-oxooxazolidin-5-yl]methoxybenzaldehyde, instead of Compound [60], whereby the title compound was obtained in a yield of 89%.

$^1$H-NMR spectrum (DMSO-d$_6$) δ:
4.03(1H,dd,J=9.2,6.2 Hz),
4.33(1H,dd,J=9.2,9.2 Hz),
4.41(1H,dd,J=11.2, 3.3 Hz) ,
4.47(1H,dd,J=11.2,3.3 Hz),
5.15(1H,m), 7.16(2H,d,J=8.9 Hz),
7.82(2H,d,J=8.9 Hz), 7.88(2H,d,J=8.9 Hz),
7.96(2H,d,J=8.9 Hz), 9.88(1H,s),
9.94 (1H, s).

The chemical formula of Compound [38] and its data such as physical properties are shown in Table 5.

(2) Synthesis of compounds of the formula (16)

(Method C)

Referential Example 19

Synthesis of 4-[3-(2-pyridyl)-2-oxooxazolidin-5-yl]methoxyaniline [88]

To a solution of 4.64 g of 4-[3-(2-pyridyl)- 2-oxooxazolidin-5-yl]methoxynitrobenzene in 50 ml of 1,4-dioxane and 150 ml of N,N-dimethylformamide, 0.47 g of 10% palladium carbon was added, followed by stirring for 2.5 hours at room temperature and 5 atm. pressure under a hydrogen stream. The reaction mixture was filtered and the filtrate was then concentrated under reduced pressure. Methanol was added to the residue and the crystals so precipitated were collected by filtration, whereby 3.41 g of the title compound were obtained (yield: 81%).

$^1$H-NMR spectrum (DMSO-d$_6$) δ:
4.02(1H,dd,J=10.2,6.6 Hz), 4.08(1H,dd,J=11.2,5.3 Hz),
4.15(1H,dd,J=11.2,3.3 Hz),
4.29 (1H,dd,J=10.2,9.2 Hz),
4.66(2H,s), 5.00(1H,m),
6.50(2H,d,J=8.9 Hz),
6.67 (2H, d,J=8.9 Hz),
7.14(1H,dd,J=7.3,5.0 Hz),
7.85(1H,ddd,J=8.6,7.3,1.0 Hz),
8.10(1H,d,J=8.6 Hz),
8.37(1H,dd,J=5.0,1.0 Hz).

Referential Example 20

Synthesis of methyl 3-(4-[3-(2-pyridyl)-2-oxooxazolidine-5-yl]methoxyphenyl)-2-bromopropionate [88]

To a solution of 3.30 g of Compound [88], which had been obtained in Referential Example 19, in 40 ml of methanol, 10 ml of acetone and 8.0 g of 47% aqueous hydrobromic acid, 0.90 g of sodium nitrite was added, followed by stirring for 0.5 hour under ice cooling. The reaction mixture was added with 6.4 ml of methyl acrylate and then, at 40° C., with 256 mg of cuprous oxide, followed by stirring for 20 minutes at the same temperature. The reaction mixture was concentrated under reduced pressure. The residue so obtained was extracted with ethyl acetate. The extract was washed successively with aqueous ammonia and brine, dried over magnesium sulfate and then filtered. The filtrate was concentrated under reduced pressure. The residue was purified by subjecting same to chromatography on a silica gel column using gradient elution with hexane-ethyl acetate, whereby 2.7 g of the title compound were obtained in the form of an oil (yield: 53%).

The chemical formulas of Compounds [88] and [89] and their data such as physical properties are shown in Table 16.

TABLE 16

| Comp'd. No. | R' | Melting point (°C.) | Yield (%) | Elemental analysis (%) or $^1$H-NMR, Calculated (Found) (DMSO-$d_6$) δ: | | |
|---|---|---|---|---|---|---|
| | | | | C | H | N |
| 88 | —NH$_2$ | 141–143 | 81 | 63.15 (63.05 | 5.30 5.35 | 14.73 14.65) |
| 89 | —CH$_2$CHCOCH$_3$ with Br, O | Oil | 53 | 3.18(1H, dd), 3.40(1H, dd), 3.72(3H, s), 4.2–4.45(4H, m), 5.02(1H, m), 6.79(2H, d), 7.05(1H, dd), 7.39(2H, d), 7.73(1H, ddd), 8.24(1H, d), 8.34(1H, dd), | | |
| 90 | —CH$_2$–S–(C=O)–NH–(C=NH)– | 219–221 | 76 | 57.28 (57.10 | 4.55 4.42 | 14.06 13.93) |
| 91. | —CH$_2$–S–(C=O)–NH–(C=O)– | 150–152 (.2/5HCl) | 58 | 55.12 (55.26 | 4.24 4.20 | 10.15 10.13) |

(3) Respective conversion from compounds of the formula (6) to compounds of the formula (1-a) and (1-b)

Example 1

Synthesis of 5-{4-[(4S,5S)-(−)-3-(4-methoxyphenyl)-4-methyl-2-oxooxazolidin-5-yl]methoxy}benzylidene-2,4-thiazolidindione [86]

A solution of 0.64 g of Compound [85] obtained in Referential Example 15, 0.26 g of 2,4-thiazolidinedione and 0.31 g of sodium acetate in 5 ml of toluene was heated under reflux for 4 hours. The reaction mixture was distilled off, followed by the addition of 4 ml of 75% aqueous acetic acid. The crystals so precipitated were collected by filtration, whereby 0.70 g of the title compound was obtained (yield: 85%).

Specific rotation: $[\alpha]_D^{25}$=−97.60° (c=1.0, DMF)

$^1$H-NMR spectrum (DMSO-d$_6$) δ:

1.26(3H,d,J=6.3 Hz), 3.77 (3H,s), 4.3–4.5(3H,m), 4.62(1H,m), 6.99(2H,d,J=8.9 Hz), 7.16(2H,d,J=8.9 Hz), 7.35(2H,d,J=8.9 Hz), 7.59(2H,d,J=8.9 Hz), 7.77(1H,s), 12.53(1H,s).

The chemical formula of Compound [86] and its data such as physical properties are shown in Table 15.

Example 2

In a similar manner to Example 1 except for the substitution of the starting material by suitable ones, Compounds [92]–[163] shown in Tables 17–27 were obtained.

TABLE 17

| Comp'd. No. | R$^1$ | R$^2$ | R$^3$ | Melting point (°C.) | Yield (%) | Elemental analysis (%) Calculated (Found) | | |
|---|---|---|---|---|---|---|---|---|
| | | | | | | C | H | N |
| 92 | 4-OMe | H | H | 224–226 | 58 | 59.15 (59.50 | 4.25 4.48 | 6.57 6.40) |
| 93 | 3-OMe | H | H | 252–254 | 46 | 59.15 (59.64 | 4.25 4.32 | 6.57 6.37) |
| 94 | 2-OMe | H | H | 221–223 | 40 | 59.15 (59.02 | 4.25 4.30 | 6.57 6.49) |
| 95 | 2-OMe | 4-OMe | H | 225–227 | 79 | 57.89 (57.67 | 4.41 4.23 | 6.14 6.11) |
| 96 | 4-OEt | H | H | 223–225 | 90 | 59.99 (60.02 | 4.58 4.62 | 6.36 6.29) |
| 97 | 2-OEt | H | H | 177–178 | 82 | 59.99 (59.75 | 4.58 4.61 | 6.36 6.20) |
| 98 | 4-Cl | H | H | 220–223 | 83 | 55.75 (55.79 | 3.51 3.66 | 6.50 6.43) |
| 99 | 2-F | 4-Br | H | 243–244 | 67 | 48.70 (48.88 | 2.86 3.01 | 5.68 5.64) |
| 100 | 4-F | H | H | 211–213 | 87 | 57.97 (58.03 | 3.65 3.53 | 6.76 6.71) |
| 101 | 2-F | 4-F | H | 201–202 | 79 | 55.56 (55.77 | 3.26 3.31 | 6.48 6.37) |
| 102 | 2-F | 4-F | 6-F | 253–255 | 76 | 53.34 (53.43 | 2.91 2.92 | 6.22 6.04) |

TABLE 18
| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 103 | 3-F | 4-F | H | 215–217 | 80 | 55.56 (55.59 | 3.26 3.26 | 6.48 6.39) |
| 104 | 2-Cl | 4-Cl | H | 255–257 | 94 | 51.63 (51.58 | 3.03 3.01 | 6.02 5.84) |
| 105 | 3-Cl | 4-Cl | H | 233–234 | 83 | 51.63 (51.72 | 3.03 3.19 | 6.02 6.03) |
| 106 | 3-F | H | H | 240–242 | 93 | 57.97 (57.92 | 3.65 3.69 | 6.76 6.66) |
| 107 | 2-Cl | H | H | 233–234 | 75 | 55.75 (56.18 | 3.51 3.52 | 6.50 6.32) |
| 108 | 2-F | 4-Cl | H | 228–230 | 74 | 53.52 (53.72 | 3.14 3.08 | 6.24 6.13) |
| 109 | 4-COOEt | H | H | 232–234 | 82 | 58.97 (59.20 | 4.30 4.32 | 5.98 5.86) |
| 110 | H | H | H | 245–246 | 58 | 60.60 (60.83 | 4.07 4.27 | 7.07 7.01) |
| 111 | 4-Me | H | H | 236–237 | 86 | 61.45 (61.67 | 4.42 4.72 | 6.83 6.76) |
| 112 | 4-Et | H | H | 235–237 | 89 | 62.25 (62.21 | 4.75 4.86 | 6.60 6.47) |
| 113 | 4-iso-Pr | H | H | 201–202 | 82 | 63.00 (63.18 | 5.06 5.52 | 6.39 6.32) |
TABLE 19
| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 114 | 3,4-(CH₂)₃- | | H | 224–226 | 82 | 63.29 (63.05 | 4.62 4.64 | 6.42 6.27) |
| 115 | 4-NMe₂ | H | H | 274–276 | 66 | 60.13 (60.38 | 4.82 4.96 | 9.56 9.10) |
| 116 | 4-O-iso-Pr | H | H | 227–229 | 90 | 60.78 (60.66 | 4.88 4.89 | 6.16 6.04) |
| 117 | 4-OCF₃ | H | H | 179–181 | 89 | 52.50 (52.20 | 3.15 3.21 | 5.83 5.54) |
| 118 | 4-CF₃ | H | H | 193–194 (·½H₂O) | 91 | 53.28 (53.26 | 3.41 3.47 | 5.92 5.74) |
| 119 | 3-CF₃ | H | H | 178–180 | 69 | 54.31 (54.80 | 3.26 3.24 | 6.03 5.77) |
| 120 | 2-CF₃ | H | H | 183–185 | 58 | 54.31 (54.28 | 3.26 2.85 | 6.03 5.96) |

TABLE 19-continued
| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 121 | 3,4-  | | H | 257–259 | 91 | 57.27 (57.04 | 3.66 3.67 | 6.36 6.20) |
| 122 | 3,4-  | | H | 263–265 | 92 | 58.15 (57.94 | 3.99 4.05 | 6.16 5.89) |
| 123 | 4- (pyridyl) | H | H | 267–270 (.1/2H₂O) | 52 | 58.47 (58.37 | 3.84 3.71 | 8.89 8.53) |
TABLE 20
| Comp'd. No. | R¹ | R² | R³ | Melting point (°C.) | Yield (%) | Elemental analysis (%) or ¹H-NMR, Calculated (Found) (DMSO-d₆) δ: | | |
|---|---|---|---|---|---|---|---|---|
| | | | | | | C | H | N |
| 124 | 4-NO₂ | H | H | 261–263 | 83 | 54.42 (54.58 | 3.43 3.46 | 9.52 9.09) |
| 125 | 4-CN | H | H | 141–143 | 65 | 3.99(1H, dd), 4.29(1H, dd), 4.35(1H, dd), 4.41(1H, dd), 5.13(1H, m), 7.12(2H, d), 7.57(2H, d), 7.76(1H, s), 7.78(2H, d), 7.89(2H, d), 12.54(1H, s) | | |
| 126 | 4- (thiazolidinedione-ethylidene) | H | H | 297–299 | 66 | 55.06 (55.38 | 3.27 3.36 | 8.03 7.56) |

TABLE 21

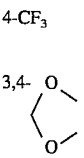

| Comp'd. No. | R¹ | R² | R⁵ | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|---|
| | | | | | | | C | H | N |
| 127 | 4-CF₃ | H | H | −104.87° (1.0, DMF) | 212–214 (½H₂O) | 83 | 53.28 (53.46 | 3.41 3.29 | 5.92 5.99) |
| 128 | 4-OMe | H | H | −113.10° (1.0, DMF) | 219–222 (¹⁄₁₀H₂O) | 90 | 58.90 (59.03 | 4.28 4.77 | 6.54 6.53) |
| 129 | 4-Cl | 2-F | H | −98.01° (1.0, DMF) | 197–199 | 89 | 53.52 (53.57 | 3.14 2.94 | 6.24 6.20) |
| 130 | 4-F | 3-F | H | −104.00° (1.0, DMF) | 233–235 | 92 | 55.56 (55.66 | 3.26 3.09 | 6.48 6.45) |
| 131 | 4-OMe | H | Me | −121.18° (1.0, DMF) | 207–208 | 84 | 59.99 (60.12 | 4.58 4.56 | 6.36 6.27) |
| 132 | 4-OCF₃ | H | H | −91.38° (1.01, DMF) | 192–194 | 86 | 52.50 (52.46 | 3.15 3.15 | 5.83 5.79) |

TABLE 22

| Comp'd. No. | R¹ | R² | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|
| | | | | | | C | H | N |
| 133 | 4-OMe | H | −21.96° (1.00, DMF) | 199–201 | 95 | 59.99 (60.04 | 4.58 4.52 | 6.36 6.35) |
| 134 | 4-Cl | 2-F | −22.29° (1.00, DMF) | 209–210 | 91 | 54.49 (54.59 | 3.48 3.34 | 6.05 6.04) |
| 135 | 4-CF₃ | H | −13.76° (1.01, DMF) | 199–202 | 92 | 55.23 (55.25 | 3.58 3.36 | 5.86 5.83) |
| 136 | 3,4-OCH₂O | | −12.99° (1.00, DMF) | 231–233 | 94 | 58.15 (58.21 | 3.99 3.84 | 6.16 6.08) |
| 137 | 4-OEt | H | −13.72° (1.02, DMF) | 188–189 | 94 | 60.78 (60.95 | 4.88 4.81 | 6.16 6.17) |
| 138 | 4-Et | H | −14.40° (1.02, DMF) | 183–185 | 94 | 63.00 (62.72 | 5.06 4.91 | 6.39 6.34) |
| 139 | 4-OCF₃ | H | −11.48° (1.01, DMF) | 178–180 | 74 | 53.44 (53.10 | 3.47 3.36 | 5.67 5.56) |

TABLE 23

| Comp'd. No. | R¹ | R² | R⁵ | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|---|
| | | | | | | | C | H | N |
| 140 | 4-CF₃ | H | H | 106.22° (1.0, DMF) | 209–211 (⅔H₂O) | 88 | 53.08 (53.21 | 3.44 3.46 | 5.89 5.60) |
| 141 | 4-OMe | H | H | 111.00° (1.0, DMF) | 217–219 | 85 | 59.15 (59.29 | 4.25 4.67 | 6.57 6.38) |
| 142 | 4-Cl | 2-F | H | 98.80° (1.0, DMF) | 195–197 | 87 | 53.52 (53.52 | 3.14 2.94 | 6.24 6.17) |
| 143 | 4-F | 3-F | H | 102.00° (1.0, DMF) | 235–237 | 90 | 55.56 (55.58 | 3.26 3.08 | 6.48 6.44) |
| 144 | 4-OMe | H | Me | 116.30° (1.0, DMF) | 207–208 | 85 | 59.99 (60.03 | 4.58 4.53 | 6.36 6.23) |
| 145 | 4-OEt | H | H | 110.30° (1.0, DMF) | 205–207 | 87 | 59.99 (59.98 | 4.58 4.81 | 6.36 6.40) |
| 146 | 4-OCF₃ | H | H | 94.19° (1.00, DMF) | 192–193 | 87 | 52.50 (52.44 | 3.15 3.08 | 5.83 5.82) |
| 147 | 3,4-OCH₂O | | H | 93.86° (1.01, DMF) | 246–247 | 92 | 57.27 (57.23 | 3.66 3.54 | 6.36 6.32) |

TABLE 24

| Comp'd. No. | R¹ | R² | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|
| | | | | | | C | H | N |
| 148 | 4-CF₃ | H | 7.80° (1.00, DMF) | 204–206 | 85 | 55.23 (55.41 | 3.58 3.50 | 5.86 5.85) |
| 149 | 4-OMe | H | 12.07° (1.01, DMF) | 179–182 | 96 | 59.99 (59.92 | 4.58 4.44 | 6.36 6.36) |

TABLE 25

[Structure: R-N containing oxazolidinone ring with B-O-phenyl-CH=C(thiazolidinedione)]

| Comp'd. No. | R | B | Melting point (°C.) | Yield (%) | Elemental analysis (%) or ¹H-NMR, Calculated (Found) (DMSO-d₆) δ: |
|---|---|---|---|---|---|
| 150 | Cl-C₆H₄-CH₂CH₂- | -CH₂- | Oil | 47 | 2.83(2H, t), 3.45(2H, m), 3.66(1H, dd), 4.10(1H, dd), 4.21(1H, dd), 4.84(1H, m), 7.08(2H, d), 7.30(2H, d), 7.35(2H, d), 8.58(2H, d), 7.77(1H, s), 12.53(1H, s) |
| 151 | MeO-C₆H₄- | -CH₂CH₂- | 209–211 | 80 | C: 59.99 (60.06), H: 4.58 (4.55), N: 6.36 (6.29) |
| 152 | CF₃-C₆H₄- | -CH₂CH₂- | 215–218 | 58 | C: 55.23 (55.38), H: 3.58 (3.52), N: 5.86 (5.62) |
| 153 | 3-pyridyl | -CH₂- | 255–257 (.3/10H₂O) | 59 | C: 56.65 (56.71), H: 3.90 (3.76), N: 10.43 (9.99) |
| 154 | 4-pyridyl | -CH₂- | >300 | 39 | 3.95(1H, dd), 4.25(1H, dd), 4.35(1H, dd), 4.42(1H, dd), 5.14(1H, m), 7.12(2H, d), 7.57(2H, d), 7.59(2H, d), 7.76(1H, s), 8.52(2H, d) |
| 155 | 3-Cl,4-F-C₆H₃- | -CH₂CH₂- | 215–217 | 92 | C: 54.49 (54.61), H: 3.48 (3.44), N: 6.05 (5.96) |
| 156 | 3,4-F₂-C₆H₃- | -CH₂CH₂- | 158–159 | 77 | C: 56.50 (56.82), H: 3.61 (3.55), N: 6.27 (6.25) |
| 157 | CF₃O-C₆H₄- | -CH₂CH₂- | 191–193 | 72 | C: 53.44 (53.61), H: 3.47 (3.46), N: 5.67 (5.66) |

TABLE 26

[Chemical structure: R-NH-C(O)-O-CH2-CH(-)-CH2-O-C6H4-CH=C(S-C(O)-NH-)-C(O)-O]

| Comp'd. No. | R | Specific rotation $[\alpha]_D^{25}$ (concentration, solvent) | Melting point (°C.) | Yield (%) | Elemental analysis (%) Calculated (Found) | | |
|---|---|---|---|---|---|---|---|
| | | | | | C | H | N |
| 158 | [3-pyridyl] | −88.40° (0.5, DMF) | 280–282 | 41 | 57.42 (57.34 | 3.80 3.77 | 10.57 10.25) |
| 159 | [6-methoxy-3-pyridyl, MeO] | −104.85° (1.1, DMF) | 228–230 | 86 | 56.20 (55.79 | 4.01 3.99 | 9.83 9.58) |
| 160 | [pyrazinyl] | −103.19° (1.0, DMSO) | 287–289 (1/5H₂O) | 73 | 53.78 (53.75 | 3.61 3.35 | 13.94 13.87) |

TABLE 27

[Chemical structure: R-NH-C(O)-O-CH2-CH(·····)-CH2-O-C6H4-CH=C(S-C(O)-NH-)-C(O)-O]

| Comp'd. No. | R | Specific rotation $[\alpha]_D^{25}$ (concentration, solvent) | Melting point (°C.) | Yield (%) | Elemental analysis (%) Calculated (Found) | | |
|---|---|---|---|---|---|---|---|
| | | | | | C | H | N |
| 161 | [3-pyridyl] | 111.19° (0.5, DMF) | 284–286 (.1/4H₂O) | 94 | 57.42 (57.30 | 3.80 3.72 | 10.57 10.50) |
| 162 | [6-methoxy-3-pyridyl, MeO] | 105.60° (1.1, DMF) | 228–230 | 80 | 56.20 (56.27 | 4.01 3.91 | 9.83 9.79) |
| 163 | [pyrazinyl] | 113.60° (1.0, DMSO) | 289–291 | 61 | 54.27 (54.14 | 3.54 3.38 | 14.06 14.05) |

Example 3

Synthesis of 5-{4-[(4S,5S)-(−)-3-(4-methoxyphenyl)-4-methyl-2-oxooxazolidin-5-yl]methoxy}benzyl-2,4-thiazolidinedione [87]

To a solution of 0.65 g of Compound [86], which had been obtained in Example 1, in 70 ml of 1,4dioxane, 2.0 g of 7.5% palladium carbon were added, followed by stirring at 50° C. and 50 atmospheric pressure for 6 hours under a hydrogen stream. The reaction mixture was filtrated and the filtrate was concentrated under reduced pressure, whereby 400 mg of the title compound were obtained as a foam (yield: 62%).

Specific rotation: $[\alpha]_D^{25} = -67.25°$ (c=1.0, DMF)
$^1$H-NMR spectrum (CDCl$_3$) δ:

1.37(3H,d,J=6.3 Hz),
3.16 (1H,dd,J=14.2,9.2 Hz),
3.44 (1H,ddd,J=14.2,4.0,2.3 Hz),
3.82 (3H,s), 4.22 (2H,d,J=4.3 Hz),
4.37 (1H,dq,J=6.0,6.3 Hz),
4.48 (1H,dt,J=6.0,4.3 Hz),
4.52(1H,dd,J=9.2,4.0 Hz),
6.88(2H,d,J=8.6 Hz),
6.93(2H,d,J=9.0 Hz), 7.17(2H,d,J=8.6 Hz),
7.31(2H,d,J=9.0 Hz).

The chemical formula of Compound [87] and its data such as physical properties are shown in Table 15.

Example 4

Compounds [164]–[196] and [200]–[236] whose chemical formulas and data such as physical properties are shown in Tables 28–37 were synthesized in a similar manner to Example 3 except for the substitution of the starting material by suitable ones.

TABLE 28

| Comp'd. No. | R$^1$ | R$^2$ | R$^3$ | Melting point (°C.) | Yield (%) | Elemental analysis (%) Calculated (Found) | | |
|---|---|---|---|---|---|---|---|---|
| | | | | | | C | H | N |
| 164 | 4-OMe | H | H | 153–155 | 69 | 58.87 (59.37 | 4.70 4.88 | 6.54 6.39) |
| 165 | 3-OMe | H | H | 122–124 | 42 | 58.87 (58.61 | 4.70 5.02 | 6.54 6.12) |
| 166 | 2-OMe | H | H | Foam | 49 | 58.87 (58.37 | 4.70 5.03 | 6.54 6.14) |
| 167 | 2-OMe | 4-OMe | H | 172–174 | 24 | 57.63 (57.65 | 4.83 4.95 | 6.11 6.21) |
| 168 | 4-OEt | H | H | 152–154 | 71 | 59.72 (59.65 | 5.01 5.03 | 6.33 6.27) |
| 169 | 2-OEt | H | H | Foam | 74 | 59.72 (59.32 | 5.01 5.10 | 6.33 6.12) |
| 170 | 4-Cl | H | H | 172–174 | 71 | 55.49 (55.93 | 3.96 3.93 | 6.47 6.50) |
| 171 | 4-F | H | H | 147–149 | 72 | 57.69 (57.98 | 4.11 3.93 | 6.73 6.70) |
| 172 | 2-F | 4-F | H | 85–88 | 60 | 55.30 (55.30 | 3.71 3.77 | 6.45 6.41) |
| 173 | 2-F | 4-F | 6-F | Foam | 87 | 53.10 (52.89 | 3.34 3.42 | 6.19 6.02) |
| 174 | 3-F | 4-F | H | 175–177 | 70 | 55.30 (55.31 | 3.71 3.72 | 6.45 6.38) |
| 175 | 2-Cl | 4-Cl | H | 177–179 | 45 | 51.40 (51.54 | 3.45 3.39 | 5.99 5.97) |
| 176 | 3-Cl | 4-Cl | H | 150–152 | 56 | 51.40 (51.57 | 3.45 3.51 | 5.99 5.96) |

TABLE 29
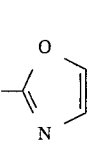
| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 177 | 3-F | H | H | 148–150 | 39 | 57.69 (57.37 | 4.11 4.22 | 6.73 6.60) |
| 178 | 2-Cl | H | H | 149–151 | 46 | 55.49 (55.23 | 3.96 3.85 | 6.47 6.40) |
| 179 | 2-F | 4-Cl | H | 135–137 | 77 | 53.28 (53.27 | 3.58 3.52 | 6.21 6.21) |
| 180 | 4-COOEt | H | H | 134–136 | 74 | 58.72 (58.72 | 4.71 5.12 | 5.95 5.90) |
| 181 | 4-(2-methyl-oxazolyl) | H | H | 280–282 | 34 | 58.44 (58.79 | 4.22 3.90 | 8.89 8.65) |
| 182 | H | H | H | 165–168 | 44 | 60.29 (60.23 | 4.55 4.42 | 7.03 7.05) |
| 183 | 4-Me | H | H | 188–189 | 74 | 61.15 (61.66 | 4.89 4.91 | 6.79 6.64) |
| 184 | 4-Et | H | H | 179–181 | 75 | 61.96 (61.96 | 5.20 5.11 | 6.57 6.60) |
| 185 | 4-iso-Pr | H | H | 163–165 | 76 | 62.71 (63.11 | 5.49 5.59 | 6.36 6.27) |
| 186 | 3,4-(cyclopentyl) | | H | 179–181 | 28 | 63.00 (63.10 | 5.06 4.97 | 6.39 6.22) |
| 187 | 4-NMe₂ | H | H | 143–145 | 40 | 59.85 (60.00 | 5.25 5.40 | 9.52 9.29) |
TABLE 30
| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 188 | 4-O-iPr | H | H | 193–195 | 74 | 60.51 (60.46 | 5.30 5.36 | 6.14 6.07) |
| 189 | 4-OCF₃ | H | H | 152–154 | 38 | 52.28 (52.49 | 3.55 3.58 | 5.81 5.75) |
| 190 | 4-CF₃ | H | H | 151–153 | 82 | 54.08 (54.25 | 3.67 3.66 | 6.01 5.92) |
| 191 | 3-CF₃ | H | H | Foam | 66 | 54.08 (54.29 | 3.67 3.77 | 6.01 5.72) |
| 192 | 2-CF₃ | H | H | Foam | 90 | 54.08 (53.88 | 3.67 4.19 | 6.01 6.44) |

TABLE 30-continued

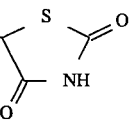

| Comp'd. No. | R¹ | R² | R³ | Melting point (°C.) | Yield (%) | Elemental analysis (%) Calculated (Found) | | |
|---|---|---|---|---|---|---|---|---|
| | | | | | | C | H | N |
| 193 | 3,4-OCH₂O- | | H | 155–157 | 68 | 57.01 (56.73 | 4.10 4.23 | 6.33 6.04) |
| 194 | 3,4-OCH₂CH₂O- | | H | 153–155 | 61 | 57.89 (57.86 | 4.42 4.49 | 6.14 5.98) |
| 195 | 4-NH₂ | H | H | 187–189 | 47 | 58.10 (58.06 | 4.63 4.51 | 10.16 9.80) |
| 196 | 4-CH(CH₂CH₃)S-C(O)NHC(O)- | H | H | 177–179 | 29 | 54.64 (54.75 | 4.01 4.37 | 7.96 8.12) |
| 197 | 4-NHAc | H | H | 158–160 | 40 | 58.01 (57.56 | 4.65 4.65 | 9.23 8.85) |
| 198 | 4-COOH | H | H | 261–263 | 66 | 57.01 (57.28 | 4.10 4.14 | 6.33 6.10) |
| 199 | 4-OH | H | H | 197–202 | 41 | 57.96 (58.08 | 4.38 4.35 | 6.76 6.52) |

TABLE 31

| Comp'd. No. | R¹ | R² | R⁵ | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|---|
| | | | | | | | C | H | N |
| 200 | 4-CF₃ | H | H | −60.06° (1.0, DMF) | 112–118 | 76 | 54.08 (54.38 | 3.67 3.83 | 6.01 5.79) |
| 201 | 4-OMe | H | H | −66.94° (1.0, DMF) | 139–142 | 70 | 58.87 (58.93 | 4.71 4.69 | 6.54 6.48) |
| 202 | 4-Cl | 2-F | H | −66.79° (1.0, DMF) | 171–173 | 80 | 53.28 (53.43 | 3.58 3.49 | 6.21 6.20) |
| 203 | 4-F | 3-F | H | −65.79° (1.0, DMF) | 158–160 | 46 | 55.30 (55.40 | 3.71 3.53 | 6.45 6.50) |
| 204 | 4-OMe | H | Me | −44.60° (1.0, DMF) | Foam | 83 | 59.72 (59.79 | 5.01 5.14 | 6.33 6.19) |
| 205 | 4-OCF₃ | H | H | −90.39° (1.01, DMF) | 130–133 | 75 | 52.28 (52.31 | 3.55 3.43 | 5.81 5.76) |

TABLE 32

| Comp'd. No. | R¹ | R² | Specific rotation $[\alpha]_D^{25}$ (concentration, solvent) | Melting point (°C.) | Yield (%) | Elemental analysis (%) Calculated (Found) C | H | N |
|---|---|---|---|---|---|---|---|---|
| 206 | 4-CF₃ | H | −5.39° (1.02, DMF) | 62–64 | 71 | 55.00 (54.70 | 3.99 4.22 | 5.83 5.65) |
| 207 | 4-OMe | H | −14.25° (1.01, DMF) | 130–132 | 69 | 59.72 (59.74 | 5.01 4.95 | 6.33 6.34) |
| 208 | 4-Cl | 2-F | −12.35° (1.02, DMF) | 88–90 | 68 | 54.26 (54.02 | 3.90 3.78 | 6.03 5.98) |
| 209 | 3,4- OCH₂O | | −8.21° (1.01, DMF) | 138–140 | 61 | 57.89 (57.93 | 4.42 4.33 | 6.14 6.17) |
| 210 | 4-OEt | H | −22.13° (1.03, DMF) | 63–65 (⅗H₂O) | 70 | 59.11 (59.03 | 5.43 5.63 | 5.99 5.93) |
| 211 | 4-Et | H | −13.16° (1.01, DMF) | 88–91 | 69 | 62.71 (63.27 | 5.49 5.75 | 6.36 6.38) |
| 212 | 4-OCF₃ | H | −13.06° (1.01, DMF) | 105–107 | 60 | 53.23 (53.30 | 3.86 4.03 | 5.64 5.45) |

TABLE 33

| Comp'd. No. | R¹ | R² | R⁵ | Specific rotation $[\alpha]_D^{25}$ (concentration, solvent) | Melting point (°C.) | Yield (%) | Elemental analysis (%) Calculated (Found) C | H | N |
|---|---|---|---|---|---|---|---|---|---|
| 213 | 4-CF₃ | H | H | 71.59° (1.0, DMF) | 109–113 | 78 | 54.08 (54.26 | 3.67 3.82 | 6.01 5.93) |
| 214 | 4-OMe | H | H | 63.69° (1.0, DMF) | 139–143 | 66 | 58.87 (59.03 | 4.71 4.72 | 6.54 6.46) |
| 215 | 4-Cl | 2-F | H | 124.60° (1.0, DMF) | 169–171 | 74 | 53.28 (53.38 | 3.58 3.51 | 6.21 6.19) |
| 216 | 4-F | 3-F | H | 75.44° (1.0, DMF) | 163–165 | 54 | 55.30 (55.28 | 3.71 3.64 | 6.45 6.43) |
| 217 | 4-OMe | H | Me | 57.89° (1.0, DMF) | Foam | 83 | 59.72 (59.78 | 5.01 5.25 | 6.33 6.06) |
| 218 | 4-CF₃ | H | H | 86.33° (1.01, DMF) | 131–132 | 46 | 52.28 (52.30 | 3.55 3.69 | 5.81 5.79) |
| 219 | 4-OEt | H | H | 65.99° (1.00, DMF) | 182–184 | 78 | 59.72 (59.60 | 5.01 5.00 | 6.33 6.25) |
| 220 | 3,4- OCH₂O | | H | 59.80° (1.02, DMF) | 97–99 | 72 | 57.01 (56.55 | 4.10 4.12 | 6.33 6.28) |

TABLE 34
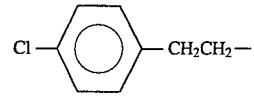
| Comp'd. No. | R¹ | R² | Specific rotation $[\alpha]_D^{25}$ (concentration, solvent) | Melting point (°C.) | Yield (%) | Elemental analysis (%) Calculated (Found) | | |
|---|---|---|---|---|---|---|---|---|
| | | | | | | C | H | N |
| 221 | 4-CF₃ | H | 2.35° (1.02, DMF) | 59–62 | 46 | 55.00 (54.63 | 3.99 4.11 | 5.83 5.69) |
| 222 | 4-OMe | H | 13.06° (1.01, DMF) | 127–129 | 65 | 59.72 (59.75 | 5.01 4.94 | 6.33 6.32) |
TABLE 35
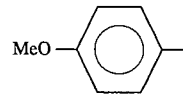
| Comp'd. No. | R | B | Melting point (°C.) | Yield (%) | Elemental analysis (%) Calculated (Found) | | |
|---|---|---|---|---|---|---|---|
| | | | | | C | H | N |
| 223 | Cl-⟨⟩-CH₂CH₂- | -CH₂- | Foam | 60 | 57.33 (56.92 | 4.59 4.66 | 6.08 5.92) |
| 224 | MeO-⟨⟩- | -CH₂CH₂- | 137–138 | 73 | 59.72 (59.56 | 5.01 5.04 | 6.33 6.30) |
| 225 | CF₃-⟨⟩- | -CH₂CH₂- | Foam | 65 | 55.00 (55.24 | 3.99 3.90 | 5.83 5.64) |
| 226 | 3-pyridyl | -CH₂- | 179–181 | 54 | 57.14 (57.04 | 4.29 4.37 | 10.52 10.51) |
| 227 | 4-pyridyl | -CH₂- | 265–267 | 47 | 57.14 (57.00 | 4.29 4.21 | 10.52 10.25) |
| 228 | Cl-⟨⟩-F | -CH₂CH₂- | 101–104 | 50 | 54.26 (54.35 | 3.90 3.92 | 6.03 5.93) |

TABLE 35-continued

[Structure: R-NH-C(=O)-O-CH(B)-O-C6H4-CH2-CH(S-C(=O)-NH-)-C(=O)-]

| Comp'd. No. | R | B | Melting point (°C.) | Yield (%) | Elemental analysis (%) Calculated (Found) | | |
|---|---|---|---|---|---|---|---|
| | | | | | C | H | N |
| 229 | 3,4-difluorophenyl | —CH₂CH₂— | 66–69 | 67 | 56.25 (55.92 | 4.05 4.23 | 6.25 6.06) |
| 230 | 4-CF₃O-phenyl | —CH₂CH₂— | 59–61 | 75 | 53.23 (53.18 | 3.86 3.75 | 5.64 5.57) |

TABLE 36

[Structure: R-NH-C(=O)-O-CH₂-CH(O-C6H4-CH2-CH(S-C(=O)-NH-)-C(=O)-)]

| Comp'd. No. | R | Specific rotation [α]$_D^{25}$ (concentration, solvent) | Melting point (°C.) | Yield (%) | Elemental analysis (%) Calculated (Found) | | |
|---|---|---|---|---|---|---|---|
| | | | | | C | H | N |
| 231 | 3-pyridyl | −78.73° (1.1, DMF) | 197–199 | 59 | 57.14 (56.97 | 4.29 4.24 | 10.52 10.41) |
| 232 | 2-MeO-5-pyridyl | −67.92° (1.1, DMF) | 157–159 | 56 | 55.94 (55.93 | 4.46 4.52 | 9.78 9.64) |
| 233 | pyrazinyl | −75.59° (1.0, DMF) | 143–145 (¼H₂O) | 14 | 53.39 (53.45 | 4.11 4.01 | 13.84 13.71) |

TABLE 37

[Structure: R-N-containing oxazolidinone linked via methoxy to phenyl-CH2-thiazolidinedione]

| Comp'd. No. | R | Specific rotation [α]$_D^{25}$ (concentration, solvent) | Melting point (°C.) | Yield (%) | Elemental analysis (%) Calculated (Found) | | |
|---|---|---|---|---|---|---|---|
| | | | | | C | H | N |
| 234 | [pyridin-3-yl] | 82.88° (1.0, DMF) | 198–200 | 57 | 57.14 (57.04 | 4.29 4.30 | 10.52 10.46) |
| 235 | MeO-[pyridinyl] | 61.69° (1.1, DMF) | 95–97 1/2dioxane | 65 | 55.81 (55.93 | 4.90 5.05 | 8.87 8.90) |
| 236 | [pyrimidinyl] | 86.59° (1.0, DMF) | 164–166 (1/10H$_2$O) | 38 | 53.75 (53.67 | 4.06 4.00 | 13.93 13.88) |

Example 5

Synthesis of 5-{4-[3-(4-acetamidephenyl)-2-oxooxazolidin-5-yl]methoxy}benzyl-2,4-thiazolidinedione [197]

To a solution of 500 mg of 5-{4-[3-(4-aminophenyl)-2-oxooxazolidin-5-yl]methoxy}benzyl-2,4-thiazolidinedione (Compound 195), which had been obtained in Example 4, in 30 ml of acetic acid, 0.14 ml of acetic anhydride was added, followed by stirring at room temperature for one hour. The reaction mixture was concentrated under reduced pressure. The residue so obtained was added with methanol to precipitate crystals. The crystals so precipitated were collected by filtration, whereby 222 mg of the title compound were obtained (yield: 40%).

$^1$H-NMR spectrum (DMSO-d$_6$) δ:
2.03(3H,s), 3.07(1H,dd,J=14.2,8.9 Hz),
3.30(1H,dd,J:=14.2,4.2 Hz),
3.90(1H,dd,J=8.9,6.6 Hz), 4.2–4.4(3H,m),
4.88(1H,dd,J:=8.9,4.2 Hz),
5.0–5.2(1H,m), 6.91(2H,d,J=8.6 Hz),
7.18(2H,d,J=8.6 Hz), 7.49(2H,d,J=9.2 Hz),
7.59(2H,d,J=9.2 Hz),
9.94(1H,s), 12.00(1H,s).

The chemical formula of Compound [197] and its data such as physical properties are shown in Table 30.

Example 6

Synthesis of 5-{4-[3-(4-carboxyphenyl)-2-oxo-oxazolidin-5-yl]methoxy}benzyl-2,4-thiazolidinedione [198]

A solution of 1.2 g of 5-{4-[3-( 4-ethoxy-carbonylphenyl)-2-oxooxazolidin-5-yl]methoxy}benzyl- 2,4-thiazolidinedione (Compound 180), which had been obtained in Example 4, in 30 ml of acetic acid and 10 ml of concentrated hydrochloric acid was heated under reflux for 21 hours. After ice cooling, the reaction mixture was added with 30 ml of water and the crystals so precipitated were collected by filtration, whereby 747 mg of the title compound were obtained (yield: 66%).

$^1$H-NMR spectrum (DMSO-d$_6$) 67 :
3.04(1H,dd,J=14.2,8.6 Hz),
3.31(1H,dd,J=14.2,4.3 Hz),
3.98(1H,dd,J=9.2,6.3 Hz) , 4.2–4.3(3H,m) ,
4.87 (1H,dd,J=8.6,4.3 Hz) , 5.08(1H,m),
6.90(2H,d,J=8.6 Hz) , 7.18(2H,d,J=8.6 Hz) ,
7.71(2H,d,J=8.9 Hz), 7.98(2H,d,J=8.9 Hz) ,
12.02(1H,s).

The chemical formula of Compound [198] and its data such as physical properties are shown in Table 30.

Example 7

Synthesis of 5-{4-[3-(4-hydroxyphenyl)- 2-oxooxazolidin-5-yl]methoxy}benzyl-2,4-thiazolidinedione [199]

The reaction was conducted in a similar manner to Example 6 except for the use of 5-{4-[3-(4-isopropoxyphenyl)- 2-oxooxazolidin-5-yl]methoxy}benzyl-2,4-thiazolidinedione (Compound 188) instead of Compound [180], whereby the title compound was obtained in a yield of 41%.

Melting point: 197°–202° C.
$^1$H-NMR spectrum ( DMSO-d$_6$ ) δ:
3.08(1H,dd,J=14.2,8.9 Hz),
3.31(1H,dd,J=14.2,4.3 Hz),
3.85(1H,dd,J=9.2,6.3 Hz) , 4.1–4.3(3H,m),
4.87(1H,dd,J=8.9,4.3 Hz), 4.99(1H,m),
6.78(2H,d,J=8.9 Hz), 6.92(2H,d,J=8.6 Hz), 7.17 (2H,d,J=8.6 Hz), 7.35(2H,d,J=8.9 Hz), 9.36(1H,s), 12.01(1H,s).

The chemical formula of Compound [199] and its data such as physical properties are shown in Table 30.

(4) Conversion from the compound represented by the formula (16) to the compounds represented by the formulas ( 1-b ) and (1-c), respectively.

Example 8

Synthesis of 5-{4-[3-(2-pyridyl)-2-oxooxazolidin-5-yl] methoxy}benzyl-2-imino-4-thiazolidinone[90]

To a solution of 2.60 g of Compound [89], which had been obtained in Referential Example 20, in 25 ml of ethanol, 545 mg of thiourea and 492 mg of sodium acetate were added, followed by heating under reflux for 22 hours. The reaction mixture was concentrated under reduced pressure. The residue so obtained was added with water to precipitate crystals. The resulting crystals were collected by filtration and then washed with ethyl acetate, whereby 1.81 g of the title compound were obtained (yield: 76%).

$^1$H-NMR spectrum (DMSO-$d_6$ ) δ:

2.84(1H,dd,J=14.2,9.6 Hz), 3.30(1H,dd,J=14.2,4.0 Hz), 4.04(1H,dd,J=10.6,6.3 Hz), 4.25–4.4(3H,m), 4.53(1H,dd,J=9.6,4.3 Hz), 5.05(1H,m), 6.87 (2H,d,J=8.9 Hz), 7.15(2H,d,J=8.9 Hz), 7.16(1H,m), 7.85(1H,ddd,J=8.6,7.6,1.0 Hz), 8.11(1H,d,J=8.6 Hz), 8.38(1H,dd,J=5.0,1.0 Hz), 8.77 (2H,s).

The chemical formula of Compound [90] and its data such as physical properties are shown in Table 16.

Example 9

Synthesis of 5-{4-[3-(2-pyridyl)-2-oxooxazolidin- 5-yl]methoxy)benzyl-2,4-thiazolidinedione [91]

A solution of 1.50 g of Compound [90], which had been obtained in Example 8, in 10 ml of 2N aqueous hydrochloric acid was heated under reflux for 30 hours. The reaction mixture was neutralized with aqueous sodium bicarbonate. The crystals so precipitated were collected by filtration and then washed with ethanol, whereby 879 mg of the title compound were obtained (yield: 58% ).

$^1$H-NMR spectrum (DMSO-$d_6$ ) δ:

3.06(1H,dd,J=14.2,8.9 Hz), 3.31(1H,dd,J=14.2,4.3 Hz), 4.03(1H,dd,J=10.2,6.4.Hz), 4.21–4.36(3H,m), 4.87(1H,dd,J=8.9,4.3 Hz), 5.06(1H,m), 6.90(2H,d,J=8.6 Hz), 7.16(1H,m), 7.17 (2H,d,J=8.6 Hz), 7.85(1H,ddd,J=8.6,7.6,1.0 Hz), 8.10(1H,d,J=8.6 Hz), 8.38(1H,dd,J=5.0,1.0 Hz), 12.01 ( 1H, s).

The chemical formula of Compound [91] and its data such as physical properties are shown in Table 16.

Preparation Example

Following are preparation examples for which Compound [179] obtained in Example 4 was employed.

Preparation Example 1: Tablets

The following ingredients, each in an amount described below, were formulated into a tablet in a manner known per se in the art.

| Ingredient | Amount |
|---|---|
| Compound | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Unsaturated fatty glyceride | 2 mg |
| Titanium dioxide | 2 mg |
| Per tablet | 300 mg |

Preparation Example 2: Granules

The following ingredients, each in an amount described below, were formulated into granules in a manner known per se in the art.

| Ingredient | Amount |
|---|---|
| Compound | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Per wrapper | 1000 mg |

Preparation Example 3: Fine subtilaes

The following ingredients, each in an amount described below, were formulated into fine subtilaes in a manner known per se in the art.

| Ingredient | Amount |
|---|---|
| Compound | 200 mg |
| Mannitol | 520 mg |
| Corn starch | 100 mg |
| Crystalline cellulose | 100 mg |
| Hydroxypropyl cellulose | 70 mg |
| Talc | 10 mg |
| Per wrapper | 1000 mg |

Preparation Example 4: Capsules

The following ingredients, each in an amount described below, were formulated into capsules in a manner known per se in the art.

| Ingredient | Amount |
|---|---|
| Compound | 100 mg |
| Lactose | 50 mg |
| Corn starch | 47 mg |
| Crystalline cellulose | 50 mg |
| Talc | 2 mg |
| Magnesium stearate | 1 mg |
| Per capsule | 300 mg |

71

Preparation Example 5: Medicated syrups

The following ingredients, each in an amount described below, were formulated into a medicated syrup in a manner known per se in the art.

| Compound | 1 g |
| --- | --- |
| Purified sucrose | 60 g |
| Ethyl parahydroxybenzoate | 5 mg |
| Butyl parahydroxybenzoate | 5 mg |
| Flavor | q.s. |
| Coloring agent | q.s. |
| Purified water | q.s. |
| Total quantity | 100 ml |

Preparation Example 6: Injections

The following ingredients, each in an amount described below, were formulated into an injection in a manner known per se in the art.

| Compound | 100 mg |
| --- | --- |
| Distilled water for injection | q.s. |
| per ampul | 2 ml |

Preparation Example 7: Suppositories

The following ingredients, each in an amount described below, were formulated into a suppository in a manner known per se in the art.

| Compound | 100 mg |
| --- | --- |
| "Witepsol W-35" | 1400 mg |
| (registered trademark; a mixture of mono, di- and tri-glycerides of saturated fatty acids ranging from lauric acid to stearic acid; product of Dynamit Nobel Corp.) | |
| Per suppository | 1500 mg |

Pharmacological Test

Test (blood-sugar lowering effect for mouse)

Each test compound was suspended in a 0.5% (W/V) hydroxypropyl methyl cellulose (HPMC) solution to give a concentration of 2.5 mg/ml (or a concentration of 0.75 mg/ml in the case of Compounds [232] and [234]). To 8–10 week old, male KK-A$^y$ mice (purchased from Nippon Clea Inc.; 6 mice a group), the resulting suspension was forcedly administered p.o. at a rate of 0.1 ml per 10 g body weight, by using an oral feeding tube. The administration of the test compound was conducted twice a day, that is, in the morning and in the evening and was continued for 5 straight days. Blood samples were collected from the candal vein of each mouse the day before the test was started and the day after the administration was finished. Each of them was placed in a blood-collecting tube in which heparin had been added beforehand. Blood sugar level of each mouse was measured by the glucose oxidase method.

From the blood sugar levels of the medicine-administered group and the control, a blood-sugar lowering rate was calculated in accordance with the following equation:

72

$$\left[1 - \frac{\text{Blood sugar level of the medicine-administered group}}{\text{Blood sugar level of the control}}\right] \times 100$$

The measurement results are shown in Table 38.

TABLE 38

| Test compound (Comp'd No.) | Blood sugar lowering rate (%) |
| --- | --- |
| 168 | 50 |
| 179 | 62 |
| 183 | 43 |
| 187 | 43 |
| 193 | 44 |
| 200 | 54 |
| 201 | 53 |
| 203 | 65 |
| 204 | 46 |
| 213 | 46 |
| 214 | 42 |
| 224 | 41 |
| 232 | 24 |
| 234 | 37 |

Industrial Applicability

Each thiazolidine derivative or a salt thereof according to the present invention has excellent blood-sugar lowering action and blood-lipid lowering action. It has good absorption into the body and has long lasting drug efficacy. In addition, it has excellent excretion and low toxicity against the human body, so that it is useful as pharmaceuticals such as a diabetes treating agent, a hyperlipidemia treating agent, an arteriosclerosis preventive and treating agent and an obesity preventive drug.

We claim:

1. A thiazolidine derivative represented by the following formula (1):

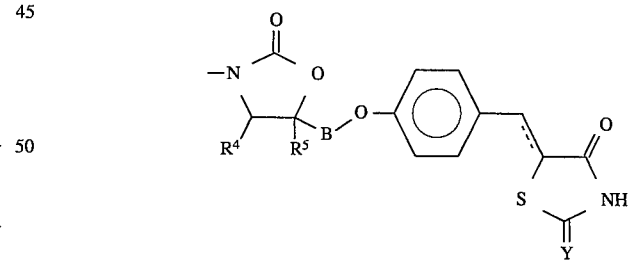

wherein $R^1$, $R^2$ and $R^3$ may be the same or different and individually represent a hydrogen atom, a halogen atom, a lower alkyl group or lower alkoxyl group which may be substituted by one or more halogen atom(s), a hydroxyl group, a nitro group, an amino group, a lower acylamino group, a mono- or di-lower alkylamino group, a carboxyl group, a lower alkoxycarbonyl group, a cyano group, a 2-oxazolylgroup, athiazolidine-2,4-dion-5-ylidenemethyl group or a thiazolidine-2,4-dion-5-ylmethyl group and $R^1$ and $R^2$ may be coupled together to form an alkylene chain —$(CH_2)_p$— wherein p stands for 3, 4 or 5 or an alkylene-dioxy chain —$O(CH_2)_qO$— wherein q stands for 1, 2 or 3, thereby forming a ring; $R^4$ and $R^5$ may be the same or different and individually represent a hydrogen atom or a lower alkyl group; each X, which may be the same or different, represents a carbon atom or nitrogen atom; Y represents an oxygen atom or an imino group; A and B individually represents a lower alkylene group; m stands for 0 or 1; and the dashed line indicates the presence or absence of a double bond;

or a salt thereof.

2. A thiazolidine derivative or a salt thereof according to claim 1, wherein $R^1$, $R^2$ and $R^3$ individually represent a hydrogen atom, a halogen atom, a lower alkyl group, a trifluoromethyl group, a lower alkoxyl group, a trifluoromethoxyl group, a hydroxyl group, a nitro group, an amino group, an acetylamino group, a dimethylamino group, a carboxyl group, an ethoxycarbonyl group, a cyano group, a 2-oxazolyl group, a thiazolidine-2,4-dion-5-ylidenemethyl group or a thiazolidine-2,4-dion-5-ylmethyl group and $R^1$ and $R^2$ may be coupled together to form a trimethylene group, methylenedioxy group or ethylenedioxy group, thereby forming a ring; $R^4$ and $R^5$ are individually a hydrogen atom or a methyl group; and A and B individually represent a methylene group or an ethylene group.

3. A thiazolidine derivative or a salt thereof according to claim 2, wherein B represents a methylene group or ethylene group; m stands for 0; $R^4$ and $R^5$ individually represent a hydrogen atom; and Y represents an oxygen atom.

4. A thiazolidine derivative or a salt thereof according to claim 3, wherein $R^1$, $R^2$ and $R^3$ individually represent a hydrogen atom, a halogen atom, a lower alkyl group, a trifluoromethyl group, a lower alkoxyl group or a trifluoromethoxyl group.

5. A pharmaceutical composition comprising an effective amount of a thiazolidine derivative or a salt thereof according to any one of claims 1 to 4 and a pharmacologically acceptable carrier.

6. A method of treatment of diabetes, which comprises administering to a patient an effective amount of a thiazolidine derivative or a salt thereof according to any one of claims 1–4.

* * * * *